United States Patent
Rodier

(10) Patent No.: US 7,985,949 B2
(45) Date of Patent: Jul. 26, 2011

(54) DETECTION OF ANALYTES USING ION MOBILITY SPECTROMETRY

(75) Inventor: Dan Rodier, Louisville, CO (US)

(73) Assignee: Particle Measuring Systems, Inc., Boulder, CO (US)

( * ) Notice: Subject to any disclaimer, the term of this patent is extended or adjusted under 35 U.S.C. 154(b) by 308 days.

(21) Appl. No.: 12/182,324

(22) Filed: Jul. 30, 2008

(65) Prior Publication Data
US 2009/0032701 A1    Feb. 5, 2009

Related U.S. Application Data

(60) Provisional application No. 60/952,669, filed on Jul. 30, 2007, provisional application No. 60/953,879, filed on Aug. 3, 2007, provisional application No. 60/984,804, filed on Nov. 2, 2007.

(51) Int. Cl.
*B01D 59/44* (2006.01)
*H01J 49/00* (2006.01)

(52) U.S. Cl. ........ 250/282; 250/281; 250/286; 250/287; 250/288; 250/290

(58) Field of Classification Search ................. 250/281, 250/282, 286–288, 290
See application file for complete search history.

(56) References Cited

U.S. PATENT DOCUMENTS

| | | |
|---|---|---|
| 4,311,669 A | 1/1982 | Spangler |
| 4,378,499 A | 3/1983 | Spangler et al. |
| 4,551,624 A | 11/1985 | Spangler et al. |
| 4,797,554 A | 1/1989 | Blanchard et al. |
| 4,950,893 A | 8/1990 | Reategui et al. |
| 5,021,654 A | 6/1991 | Campbell et al. |
| 5,032,721 A | 7/1991 | Bacon et al. |
| 5,095,206 A | 3/1992 | Bacon, Jr. et al. |
| 5,234,838 A | 8/1993 | Bacon, Jr. |
| 5,283,199 A | 2/1994 | Bacon, Jr. et al. |
| 5,338,931 A | 8/1994 | Spangler et al. |
| 5,405,781 A | 4/1995 | Davies et al. |
| 5,420,424 A | 5/1995 | Carnahan et al. |
| 5,455,417 A | 10/1995 | Sacristan |
| 5,457,316 A | 10/1995 | Cohen et al. |

(Continued)

FOREIGN PATENT DOCUMENTS
EP    0 596 978 B1    3/1997
(Continued)

OTHER PUBLICATIONS
International Search Report, corresponding to International Application No. PCT/US08/71535, issued Oct. 1, 2008.
(Continued)

*Primary Examiner* — Robert Kim
*Assistant Examiner* — Meenakshi S Sahu
(74) *Attorney, Agent, or Firm* — Greenlee Sullivan P.C.

(57) ABSTRACT

Methods and systems are provided for detecting analytes in a gas phase sample. An ion mobility spectrometer is provided for detecting analytes having an excess amount of dopant in its separation region. In an embodiment, the dopant is added directly to the separation region, such as with a drift gas or by diffusion, thereby providing excess dopant that dominates subsequent cluster formation and maintenance. Excess dopant in the separation region minimizes or reduces interfering signals associated with unwanted substances, such as water vapor, that are introduced to the IMS. In an aspect, the invention provides IMS systems and methods having increased sensitivity and reliability for analyte detection.

36 Claims, 15 Drawing Sheets

U.S. PATENT DOCUMENTS

| | | | |
|---|---|---|---|
| 5,476,002 A | 12/1995 | Bowers et al. | |
| 5,491,337 A | 2/1996 | Jenkins et al. | |
| 5,661,226 A | 8/1997 | Bowers et al. | |
| 6,225,623 B1 | 5/2001 | Turner et al. | |
| 6,291,821 B1 | 9/2001 | Danylewych-May et al. | |
| 6,495,824 B1 | 12/2002 | Atkinson | |
| 6,586,732 B2 | 7/2003 | Lee et al. | |
| 6,825,460 B2 | 11/2004 | Breach et al. | |
| 6,945,090 B2 | 9/2005 | Rodier | |
| 7,026,612 B2 | 4/2006 | Guevremont et al. | |
| 7,045,776 B2 * | 5/2006 | Kaufman et al. | 250/281 |
| 7,057,168 B2 | 6/2006 | Miller et al. | |
| 7,129,479 B2 | 10/2006 | Carroll et al. | |
| 7,129,482 B2 | 10/2006 | Miller et al. | |
| 7,164,122 B2 | 1/2007 | Fuhrer et al. | |
| 7,208,123 B2 | 4/2007 | Knollenberg et al. | |
| 7,235,214 B2 | 6/2007 | Rodier et al. | |
| 2003/0235926 A1 | 12/2003 | Knollenberg et al. | |
| 2005/0028593 A1 | 2/2005 | Rodier | |
| 2005/0051719 A1 | 3/2005 | Miller et al. | |
| 2005/0173629 A1 | 8/2005 | Miller et al. | |
| 2005/0253061 A1 | 11/2005 | Cameron et al. | |
| 2007/0029477 A1 * | 2/2007 | Miller et al. | 250/290 |

FOREIGN PATENT DOCUMENTS

| | | |
|---|---|---|
| EP | 0 604 528 B1 | 11/1997 |
| EP | 1 650 545 | 4/2006 |
| WO | WO 93/03360 | 2/1993 |
| WO | WO 93/06476 | 4/1993 |
| WO | WO 96/28728 | 9/1996 |
| WO | WO 96/37773 | 11/1996 |
| WO | WO 00/79261 | 12/2000 |
| WO | WO 2005/036130 | 4/2005 |
| WO | WO 2006/114579 | 11/2006 |
| WO | WO 2006/123107 | 11/2006 |
| WO | WO 2007/066240 | 6/2007 |
| WO | WO 2007/069088 | 6/2007 |
| WO | WO 2007/080376 | 7/2007 |
| WO | WO 2007/085898 | 8/2007 |

OTHER PUBLICATIONS

Written Opinion of the International Searching Authority, Corresponding to International Application No. PCT/US08/71535, mailed Oct. 1, 2008.

Bacon, T. (2003) "Ion Mobility Spectroscopy Applications for Continuous Emission Monitoring," available at: http://www.jusun.com.tw/IMS%20Application%20for%20CEM.pdf.

Creaser et al. (2004) "Ion Mobility Spectrometry: A Review. Part 1. Structural Analysis by Mobility Measurement," *Analyst* 129:984-994.

Linker et al. (2006) "Handheld Trace Explosives Detector," Presentation given at the 4th International Aviation Security Technology Symposium, Nov. 27-Dec. 1, 2006, Washington, D.C.

Proctor et al. (1984) "Alternative Reagent Ions for Plasma Chromatography," *Anal. Chem.* 56:1794-1797.

\* cited by examiner

DETECTION OF ANALYTES USING ION MOBILITY SPECTROMETRY

CROSS-REFERENCE TO RELATED APPLICATIONS

This application claims priority under 35 U.S.C. 119(e) to U.S. Provisional Patent Applications 60/952,669 filed Jul. 30, 2007, 60/953,879 filed Aug. 3, 2007 and 60/984,804 filed Nov. 2, 2007, each of which are hereby incorporated by reference in its entirety to the extent not inconsistent with the disclosure herein.

FIELD OF THE INVENTION

Improved ion mobility spectrometers (IMS) having increased sensitivity and stability for detecting gas phase analytes are provided. In particular, high-concentration dopant is provided to the IMS system to facilitate sensitive and precise analyte detection without a need for removing substances such as water vapor that tend to interfere with analyte detection.

BACKGROUND OF THE INVENTION

The commercial importance of IMS for detecting analytes is reflected in the large number of patents related to detection of narcotics (U.S. Pat. No. 5,491,337), explosives (U.S. Pat. No. 6,225,623), contamination-indicating substances, chemical agent detection, and generally for monitoring release of hazardous gases to provide early warning of impending danger (U.S. Pat. No. 5,095,206). Contamination is a concern in many industries, ranging from the semiconductor, hard-disk drive, flat panel display, aerospace, and other high-tech industries. The damage inflicted by contamination is ubiquitous, causing problems to production processes, product material, equipment surfaces, and in serious cases can even affect human health. Accordingly, it is vital that contamination (or analytes indicative of narcotics, explosives or other hazards) be identified rapidly and reliably so that appropriate corrective steps are taken before significant damage occurs.

IMS systems are recognized for their utility in detecting analytes and can be readily deployed for continuous long-term monitoring of the surrounding environment. The general configuration of IMS systems is well known in the art, with such systems having a means for ionizing an analyte of interest and means for measuring ion mobilities by application of an electric field. Because different analytes may have different ion mobilities, IMS systems monitor and detect an analyte of interest by determining the speed with which ionized analyte moves through an applied electric field and interacts with an ion detector. There is ongoing effort to provide IMS systems having improved sensitivity and which are less prone to false positive readings, and particularly to overcome problems associated with presence of substances that may interfere with analyte monitoring and detection. As various means for increasing the sensitivity of IMS systems are developed, there is recognition that instrument selectivity can be accordingly impacted, such as by generation of anomalous peaks, charged particles and clusters thereof that can mask the signal used to detect an analyte of interest. A concern is that the analyte will not be detected, the calculated analyte concentration will be incorrect, or a false positive will trigger unnecessary action. Regardless, concern related to unreliable detection requires repeated testing and further delays in analyte detection. One technique for minimizing generation of anomalous signal from interfering substances involves introduction of dopants to the IMS.

To improve sensitivity while maintaining adequate selectivity, U.S. Pat. No. 5,491,337 proposes adding low concentration (on the order of a few ppm) of a dopant (nicotinamide vapor) to the carrier gas stream prior to introduction to the IMS detection cell (e.g., dopant is not added directly to the drift region). The dopant acts as a charge transfer mediator and assists in cleaning up the spectrum obtained in an IMS that detects narcotics obtained from air samples, thereby increasing system sensitivity. In that system, dopant is selected to exhibit proton affinity that is higher than most of the ions produced in the ionization chamber, so that a single peak is generated in the absence of narcotic vapors. The dopant molecules are preferably selected to have a basicity that is between the basicity of the hydrogen carrier and the alkaloid molecules of interest. In this manner, in the absence of non-alkaloid background at equilibrium, the ion spectrum shows only ion peaks associated with the dopant species. In the presence of narcotic vapors, charge transfer between the dopant molecules and narcotic molecules generates a population of narcotic ions which are detected. That system, however, is limited to ammonia ($NH_3$) or nicotinamide dopants added in low concentration to the carrier and sample gas stream prior to introduction to the IMS cell.

U.S. Pat. No. 6,225,623 discloses an IMS that is doped with ions produced by a corona discharge ionization source for detecting explosive compounds and narcotics. There is recognition of an interfering peak problem when an analyte is introduced to the system. In a "clean" sample (without analyte and impurities), a single reactant ion peak is observed. In contrast, when the analyte is provided multiple, overlapping peaks are detected in addition to reactant ion peak. These other peaks tend to mask the reactant ion peak and decrease IMS sensitivity, as well as present possible false-positive problems. To overcome this interfering peak problem, chemical doping is used to change the way in which sample vapor introduced to the IMS is ionized and subsequently detected. See Proctor and Todd, Alternative Reagent Ions for Plasma Chromatography. Anal. Chem. 56:1794-97 (1984). In such dopant systems, the dopant is obtained by ionization by-products of the corona discharge ionization process (e.g., corona dopant ions) or by a chemical dopant source that recirculates. Such use of dopant reportedly suppresses background contamination without significant loss of ion peaks associated with the sample of interest (analyte in that case is RDX). That IMS, however, involves complicated pneumatics and closed-loop paths for introducing chemical dopant. In addition, detection of an analyte is by introducing a sample wipe that has swabbed a surface of interest and so requires high-temperature operation to satisfactorily detect an analyte of interest. High temperatures of about 250° C. are also required to reduce or eliminate water vapor in the system that would otherwise generate interfering peaks. Such high-temperature systems present design restrictions and limits the choice of surface materials to materials capable of withstanding such high temperatures.

A different IMS system known as high field asymmetric waveform ion mobility spectrometry (FAIMS) is disclosed in U.S. Pat. No. 7,026,612. In such systems, the applied electric field is switched between high and low voltage states to generate an asymmetric voltage waveform. Many FAIMS devices use a carrier gas comprising a purified flow of nitrogen, oxygen or dehumidified air (e.g., see U.S. Pat. No. 5,420,424). The carrier gas can be dehumidified by a filter or membrane that prevents passage of water vapor to the IMS cell. U.S. Pat. No. 7,026,612 discloses use of these filters in combination with dopant mixing of the sample prior to introducing the sample to the IMS cell, and more particularly prior to ionization of the mixture. In that system, the mixture contains less than about one percent dopant gas by volume and the carrier gas itself is a doped carrier gas. The dopant is not introduced directly to the separation region of the IMS cell to be transported by drift gas to the ionization region. In embodiments of that system without a water-removing filter, the carrier gas and sample has no traces of water or other contaminates that could adversely affect sensitivity and/or separation capability. This is a recognition that such systems remain prone to water vapor-induced generation of interfering ions and ion clusters.

Other IMS systems that use dopant to improve specificity are provided in U.S. Pat. Nos. 5,095,206, 5,032,721, 5,234,838, 5,095,206 and 5,283,199. U.S. Pat. No. 5,283,199 discloses using one or more dopants (e.g., methylamine) to improve detection of chlorine dioxide. Those systems generally require a membrane to exclude interfering substances or other means for minimizing water vapor and introduce the dopant to the carrier gas containing a gaseous analyte prior to introduction to the IMS cell. Such membranes add cost to the system and require maintenance to ensure they remain capable of removing adequate amount of unwanted substances while continuing to permit passage of analyte of interest.

U.S. Pat. No. 6,495,824 discloses an IMS system having a plurality of reactant-containing reservoirs which can be reacted with a sample to form adducts with varying ion mobilities. In a similar fashion to the other IMS systems known in the art, that system also introduces reactant to the sample or is itself the carrier stream. Reactant is not added directly to the separation region.

From the forgoing, it is apparent there is a need in the art for IMS systems that avoid generation of unwanted ions and clusters thereof that affect the ability to reliably and sensitively detect analytes of interest. In such a system, the need for a water-vapor removing membrane is avoided, thereby decreasing the complexity of the system while maintaining sensitivity.

SUMMARY OF THE INVENTION

An aspect of the invention provides a device and related methods for detecting an analyte with high sensitivity. Provided are IMS systems that are sensitive, reliable and have fast response times by introducing dopants in high concentration to the separation region of an IMS system or an IMS cell. A dopant that is itself the drift gas ensures that dopant distribution in the separation region is uniform and can dominate cluster formation and/or charge transfer. Alternatively, dopant is introduced to the separation region by diffusion (e.g., without drift gas) to provide high concentration of dopant to a localized portion of the separation region, such as at the ion detector, and lower concentration at the other end of the separation region corresponding to the shutter gird. This aspect is useful during low-level analyte detection, where it can be beneficial to introduce correspondingly low-level of dopant to the analyte to increase target ion peak. Increasing dopant level in the separation region also provides, however, a number of advantages that result in improved operating characteristics. For example, high dopant levels in the separation region provides capacity for accurately detecting analytes even in the presence of relatively high water vapor levels by suppressing interfering peak signals attributed to water. High dopant in the drift or separation region maintains and/or stabilizes clusters corresponding to analytes in the separation region compared to conventional systems that often suffer signal degradation attributed to cluster breakdown and/or undesirable charge transfer reactions. Accordingly high dopant in the separation region maintains and stabilizes cluster formation, thereby improving the overall sensitivity and reliability of the measured spectrum.

In systems where dopant is only circulated through the ionization or reaction region, such as dopants that are added to the gas sample prior to or simultaneous with introduction to the ionization regions, only a fraction of dopant is ionized and directed to the separation region by the electric field. In addition to only a small fraction of ionized dopant entering the separation region, there is also constant purging of the separation region with the countercurrent drift gas flow. Accordingly, the walls of the separation region do not reach equilibrium with the dopant. Typically, the level of dopant in the separation or drift region, is on the order of parts per trillion (ppt) or less than a ppt concentration. Under these conditions, those IMS systems are not capable of driving cluster formation in the separation region with dopant (as very little or no dopant is actually in the separation region) and so there can be a large number of additional peaks detected by the instrument that consume charge but provide no useful information. In conventional IMS systems, water chemistry dominates ion cluster formation, particularly in the positive ion mode. Therefore, conventional IMS systems require membranes and high cell temperatures (>150° C.) to reduce water in the cell and related water cluster formation. Water-induced cluster formation is further minimized in those systems by introducing clean, dry air (CDA) or inert gas as the drift gas in an attempt to remove unwanted water vapor from the separation region.

In contrast, providing dopant directly to the separation region, such as dopant in excess amount or at a "high concentration" such as on the level of ppm or greater depending on the application (e.g., about $10^6$ times or more compared to the dopant level in the separation region of a conventional IMS), reduces interference while increasing sensitivity and stability. Such improvement occurs because dopant chemistry dominates cluster formation by maximizing dopant ion cluster formation within the separation region, thereby driving ion mobility peak generation even in the presence of water vapor. Accordingly, an aspect of the present invention maximizes dopant ion cluster formation. Dopant ion refers to dopant monomers, dimers, trimers, dopant-analyte adducts. Maximizing dopant ion cluster formation reduces water ion cluster formation and allows the cell to sample ambient air directly without removing water vapor. High concentration dopant in the separation region is particularly useful for cleaning up the anomalous peaks often detected in current IMS systems. The end result of such a high-concentration dopant system is the minimization and even removal of unwanted peaks from the ion mobility spectrum generated by the IMS. Dopant level in the separation region refers to both charged and neutral dopant species. In an aspect, the dopant concentration in the separation region is not uniform. In an embodiment of this aspect, dopant concentration in excess refers to a portion of the separation region having excess dopant, such as a region that contains the ion collector or detector, and other regions that optionally do not have excess dopant, such as a region adjacent to the shutter grid.

Furthermore, IMS systems having membranes to prevent entry of water vapor to the cell significantly reduces the amount of analyte in the ionization region of the IMS. Typically, only about one-third of the analyte crosses the membrane. In addition, the analyte is further diluted by about a factor of two by the drift gas. Not only does the membrane decrease the effective lower limit of analyte detection, but it also increases instrument response time. Such a membrane also adds unnecessary expense to the system and is itself a potential source of contamination that the IMS systems described herein optionally avoid. Minimizing or avoiding the problems associated with water vapor-based peak generation facilitates IMS systems where the membrane is unnecessary, thereby increasing the sensitivity of the system. In an aspect, sample gas flows directly into the cell without a membrane, thereby maximizing total analyte provided to the cell. The sample gas containing analyte in the ionization region may then be diluted by as little as about 10% by the drift gas containing dopant that has been introduced to the separation region. Dilution provides a means of selectively adjusting the dynamic range of an IMS system. For applications wherein a specific dynamic range is required, appropriate dilution of the sample is provided. In aspects where there is no drift gas, such as dopant introduction by diffusion from the dopant source, dilution of sample gas containing analyte is avoided. In this aspect, the flow of sample gas is controlled so as to match the concentration of the dopant at the first end of the separation region (e.g., at the shutter electrode), thereby providing selective adjustability of the dynamic range and sensitivity of the analyzer. Similarly, the diffusivity or flux of dopant can be adjusted so as to vary the concentration of dopant at the shutter electrode.

In an embodiment, the invention provides IMS systems and analyte detection methods wherein the separation region of an IMS is provided with a high concentration of a chemical dopant. In an aspect, the dopant is continuously introduced, thereby ensuring the cell has a continuous high concentration dopant.

Provided in IMS systems is an inlet for introducing a gas phase sample to an ionization region, a separation region, and a source of dopant capable of introducing high concentration or excess dopant to the separation region relative to analyte, for example. The ionization and separation regions are said to be in fluid communication with each other in that dopant and analyte ionized in the ionization region are capable of entering the separation region when the electrode shutter is open and an electric field applied. Similarly, in aspects having drift gas, drift gas is capable of flowing from the separation to the ionization region. An ionization source provides means for ionizing the analyte in gas phase sample and dopant in the ionization region. A detector positioned in fluid communication with the separation region is capable of collecting and detecting the ions on the basis of ion mobility, including clusters or adducts of those ions. By continuously introducing to the regions a high concentration or excess dopant, dopant and dopant ions dominate cluster formation, and thereby heavily influence the detected drift velocity peaks measured by the detector.

In an embodiment, the IMS drift gas is itself the dopant. In an embodiment, the drift gas is not the dopant, and the dopant and drift gas are mixed prior, simultaneously, or after introduction of each to the separation region. In a straightforward embodiment, the dopant and drift gas are mixed prior to introduction to the separation region, and introduced to the separation region at a dopant inlet port, thereby facilitating uniform distribution of dopant throughout the drift gas region. Alternatively, no drift gas is needed to introduce dopant to the separation region. Instead a source of dopant "passively" enters the IMS system by diffusion from the source, through the dopant inlet port and in a longitudinal direction from the ion detector to the shutter grid. In this embodiment, diffusion can be described using Fick's law, where the flux of dopant is proportional to the concentration gradient of the dopant (e.g., $J=-D_A dc/dx$, where $D_A$ is the diffusivity or diffusion coefficient of the dopant). Accordingly, different parameters are available to control the flux of dopant (and therefore the concentration of dopant at the shutter electrode and ion detector) such as the amount of dopant introduced to the system (such as by shortening and/or widening the conduit that connects the dopant source to the separation region, adjusting the temperature of the dopant permeation module, etc.).

The particular location of the dopant inlet port is governed by the geometry of the separation region. For example, for a longitudinally aligned separation region, the dopant port may be positioned at an end of the separation region furthest from ionization region and shutter electrode, such as at the ion detector. Such a configuration facilitates a counter-current flow of drift gas and dopant that is parallel and opposite to the applied electric field in the separation region. Accordingly, the direction of drift and dopant gas flow is substantially opposite to the direction of ion travel in the electric field.

An outlet may be positioned in the ionization region of any of the spectrometers or cells disclosed herein for removing unwanted or excess material (e.g., drift gas, sample, unionized material, carrier gas, etc.) from the ionization region. The spectrometer may be a single pass system, in that the dopant is not reused for subsequent measurements. In an alternative embodiment, dopant and/or drift gas that is exhausted from the ionization region may be recycled back into the system for reuse.

One advantage of systems outlined herein is that they optionally operate in a low temperature mode, such as at temperatures less than about 150° C. State-of-the art systems generally operate under high temperature conditions to facilitate reduction in unwanted signal be minimizing water vapor introduction. In an embodiment, the operating temperature is selected from a range that is between 40° C. and 60° C. In this embodiment, operating temperature refers to the average temperature during operation of a cell that contains the ionization and separation regions.

The spectrometer can operate with or without a membrane for removing potentially interfering substances. For example, the membrane may be a hydrophobic membrane for removing water vapor. Alternatively, in membrane-free systems substantially all of the analyte that is contained in the gas phase sample is introduced to the ionization region. Similarly, substantially all of the water vapor in the gas phase sample may be introduced to the ionization region. This is an improvement over state of the art IMS systems that, because of interference concerns, often lose analyte in the interference-removing process.

As known in the art, a carrier gas may be used to facilitate transport of gas phase analyte sample to the ionization region. A further characteristic of the system is related to flowrates of the various inputs. For example, the analyte introduction may be described by a sample flowrate and the dopant introduction by a dopant flowrate. Depending on the specific system configuration, these flowrates may include flow of other material such as carrier gas or drift gas. The flowrates of each may be described relative to the other. In embodiments where it is desired to not unduly dilute the introduced gas phase analyte, the sample inflow rate may be high relative to dopant inflow rate, such as greater than 75%, greater than 90%, or between about 80% and 95%. To ensure continued excess dopant in the system, the concentration of dopant introduced at the dopant inlet may be increased as the relative flowrate of dopant introduction decreases. In situations where analyte dilution is beneficial, dopant inflow may be similar or greater than sample inflow, such as 60% dopant drift gas inflow and 40% sample gas inflow, for example. In an embodiment, the dopant inflow is continuous and selected from a range that is between 20 mL/min to 1000 mL/min. Flow-rate may be used as a control to establish the sensitivity or detection range of the instrument, such as by dilution of inflow to generate a desired analyte detection range. In an aspect, any of the spectrometers or methods described herein use a sample flowrate that is a pulsed flow.

In embodiments where dopant is introduced to the system by diffusion only, without an "active" flow-rate that transports the dopant by convection, other parameters are used to describe relative amount of dopant to analyte as described hereinbelow.

There are a number of functional characteristics to describe excess dopant or high concentration dopant. The specific dopant amount depends on the operating conditions and set-up of the IMS system. Accordingly, in an embodiment the dopant excess amount is dependent on the analyte amount. In an embodiment the ratio of dopant to analyte in the reaction region or ionization region is between 1000:1 and 100:1. In the separation region, the concentration of dopant to analyte is on the order of ppm dopant to ppt analyte (e.g., a ratio on the order of $10^6$, or between $10^3$ and $10^{10}$ or higher). In an aspect, this ratio is determined in the separation region. In another embodiment, the amount of dopant may be similarly tied to potentially interfering substances, such as water vapor level in the separation region or ionization region. Dopant excess may be described in terms of an absolute amount of a concentration-defining variable. For example, in certain aspects of the invention, the dopant excess in the drift or separation region is defined as a concentration that is selected from a range that is between 0.5 ppm to 400 ppm, or 1 ppm to 350 ppm. In an embodiment, the dopant concentration is substantially constant throughout both the ionization region and the separation region. An alternative description of the amount of dopant in the system required to be considered an "excess amount" relates to providing a sufficient amount of dopant to the spectrometer region so that the dopant is in equilibrium with walls of the separation region, and particularly walls defining the drift gas region. Such equilibrium occurs when there are no longer any wall effects on the distribution of dopant in the separation region, such that the dopant level reaches a time-independent steady-state concentration level in the cell. In an embodiment, the minimum amount of dopant is determined by the variable that requires the highest dopant level. The specific value of dopant concentration to obtain excess dopant may be empirically determined by observing the measure output spectra from the IMS and accordingly depends not only on specific analyte and desired instrument sensitivity, but also on the peaks generated by interfering substances that are desirably suppressed and the desired percentage peak suppression.

In an embodiment, the dopant concentration has a substantial gradient in the separation region, ranging from a maximum concentration at the separation region end corresponding to the ion collector or detector to a minimum concentration at the separation end corresponding to the ionization region (e.g., at the shutter electrode). In this embodiment, the introduction of gas sample containing analyte to the ionization and separation region boundary provides good mixing of dopant and analyte at the shutter electrode.

In an aspect, the invention provides spectrometers with a drift gas region or separation region made of a polymeric material. Such material can facilitate decreasing instrument cost and design that may not be available in current IMS systems that have relatively high operating temperatures.

In an embodiment, the invention provides for IMS having an analyte sensitivity of at least on the order of low ppt. Alternatively, the sensitivity may be described in terms of improvement over current IMS having a membrane-containing element to remove unwanted water vapor. In this aspect, the sensitivity may be increased by a factor of at least about 2 to 3, attributed to the loss of analyte due to the membrane in current membrane-based IMS analyzers or reduction in charge-consuming interfering peaks.

In another embodiment, the presence of excess dopant is described in terms of the capability of the dopant to drive interactions within the ionization and/or separation regions. For example, the excess dopant generates dopant-dopant clusters and dopant-analyte dimerization clusters and prevents detectable formation of ion clusters from an interfering substance, such as an interfering substance that is water vapor or ion products generated via ionization of water vapor or materials that would otherwise interact with water vapor but for the excess dopant.

The devices and methods described herein are generally useful for any analyte/dopant system, so long as excess dopant is capable of being introduced to the system. In this aspect, the analyte is selected from the group consisting of bases such as ammonia and amines, hydrazines, acids such as HCl, $Cl_2$, HF, $F_2$, $Br_2$, HBr, $NO_x$, $SO_x$, pharmaceutical compounds and precursors thereof, industrial chemicals, chemical warfare agents, peroxides, explosive-indicating compounds; narcotic-indicating compounds and the dopant is selected from the group consisting of substituted phenols (for detecting acid gases such as HF, HCl, $Cl_2$, $NO_2$, $SO_2$, carbonyl sulfide, and others), DMMP (Dimethyl methylphosphonate —$CH_3PO(OCH_3)_2$), methyl salicylate, 2-hydroxyacetophenone, $SO_2$, 2-Chlorobutane. The dopant is selected depending on the analyte to be detected to ensure appropriate dopant/analyte interaction. Some examples of useful dopant/analyte pairs include, but are not limited to, DMMP/ammonia, methyl salicylate/$H_2O_2$, methyl salicylate/acids. The system may be operated in either positive ion or negative ion mode (depending on the analyte), by switching the direction of the E field. This in turn, is one factor that influences appropriate dopant selection.

In an embodiment, any of the systems and methods is for detection of analyte that is suspended in ambient air, such as an analyte that is suspended in room air. In this aspect, the sample gas phase comprises ambient air. Alternatively, the analyte may be transferred from a surface (e.g., clothing, luggage, skin) to a wipe, and subsequently introduced to the IMS of the present invention.

In a separate embodiment, the invention is generally an IMS cell having an ionization region, a separation region in fluid communication with the ionization region. Further provided are a means for introducing an analyte in a gas phase sample to the ionization region and a means for introducing a dopant in an excess amount to the separation region. The separation and ionization regions are in fluid communication with each other. Accordingly, the introduced dopant provides to at least a portion of the separation region excess dopant. In another aspect, at least a portion of the ionization region is continuously provided with excess dopant, such as a portion containing a part of the shutter electrode.

Means for introducing a dopant includes mixing dopant and drift gas in a chamber and providing the dopant and drift gas to the separation chamber. Amount of dopant introduced to the chamber may be controlled by regulators and a dopant source that generates dopant may be replenished as needed. Alternatively, dopant may be introduced to the separation region at a dopant inlet port. Optionally, an additional port introduces drift gas to the separation region and the drift gas flow in the IMS cell subsequently disperses dopant throughout the IMS system. Dopant from a dopant source may be controllably generated by any means known in the art including but not limited to a controlled addition via a chemical reservoir of dopant, permeation tubes, evaporative dopant generation and/or temperature-induced dopant generation.

Another means for introducing a dopant is by a dopant source (e.g., chemical reservoir of dopant, permeation tube, evaporative dopant generator and/or temperature-induced dopant generator) that passively diffuses from the source to the chamber. In this aspect, no drift gas is required. For example, a dopant source may be positioned in a holder, where the dopant is introduced to the separation region by a conduit that fluidly connects the holder and the separation region. Dopant introduced to the separation region can then diffuse from a high concentration region (in the immediate vicinity of where the dopant is introduced, such as at or near the ion detector) to a low concentration region (e.g., in the vicinity of the shutter electrode, where introduction of sample gas ensures that dopant concentration remains low). The air sample introduction in the region of the shutter electrode ensures this region is well-mixed and the flow of air sample into and out of this region maintains a low-level of dopant in this region.

Means for introducing an analyte in a gas phase sample includes a pump or fan for drawing a gas sample into the ionization region directly. Alternatively, the pump or fan may draw a gas sample into a region in which a carrier gas is introduced to force the sample with carrier gas into the ionization region. As known in the art, related flow controlling devices including flow regulators, diffusers, connectors, valves, etc. are provided as needed.

The ionization region of the IMS cell optionally comprises an ionization source positioned to generate ionization of the analyte and dopant in the ionization region, thereby generating detectable ions. In this aspect, an ion detector is positioned in the separation region for detecting said detectable ions on the basis of ion mobility. Typically, ion mobility is determined by monitoring a spectrum obtained from the amplitude of the detected peaks as a function of time in the separation region. As there is a characteristic drift time for particular analyte or detectable ions, analyte is detected and concentration determined based on these spectra. As discussed herein, the dopant optionally further comprises a drift gas. Any of the IMS cells disclosed herein are optionally incorporated into an IMS, as known in the art that is capable of detecting a gas phase analyte.

In another embodiment of the present invention, methods for detecting an analyte in a gas phase sample is provided. Generally, an ion mobility cell having a separation region and an ionization region in fluid communication with each other is provided. The separation region has a first end adjacent to the ionization region (e.g., at the shutter electrode that is between the separation and ionization region boundary), and a second end corresponding to the ion detector, where the ion detector faces the shutter electrode and is separated from the first end by a longitudinal distance. An analyte is introduced to the ionization region and a high concentration of dopant introduced to at least the separation region second end, or to the entire separation region. The analyte and dopant is subject to an ionizing means to generate detectable ions that are passed through the separation region. The ions (and any clusters thereof) are separated on the basis of ion mobility and detected with a detector, thereby detecting the analyte. In an embodiment, a drift gas sweeps the dopant to the ionization region, thereby establishing high levels of dopant in both the separation and ionization regions. In an embodiment, the dopant is introduced to the ionization region or shutter electrode by diffusion only.

The methods and devices claimed herein are capable detecting a wide range of analytes including, but not limited to, one or more of amines, hydrazines, chlorine, HCl, HF, $F_2$, $Br_2$, HBr, $NO_x$, $SO_x$, pharmaceutical compounds and precursors thereof, industrial chemicals, chemical warfare agents, ammonia; peroxides; explosive-indicating compounds; narcotic-indicating compounds.

In an embodiment, a drift gas is introduced to the separation region to convey (e.g., by convection) the dopant in the separation region to the ionization region. In an aspect of this embodiment, the drift gas flow provides for a substantially uniform concentration of dopant in the separation region, and optionally within the ionization region as well. In an embodiment, the dopant is introduced to the separation region by diffusion. In this aspect, a concentration gradient of dopant is established in the separation region along a longitudinal direction from the second end at the ion detector having a high concentration to the first end at the ionization region boundary (e.g., the shutter electrode) having a low dopant concentration. Optionally, one or more parameters are varied by a user of the IMS system to match dopant at the electrode shutter to analyte and/or contaminant at the electrode shutter, thereby providing a system having an adjustable dynamic range and sensitivity. For example, the amount of sample, the flux of dopant or both can be adjusted to provide a dopant to analyte ratio at the shutter electrode that is between 100:1 to 10,000:1.

Similarly, the methods and devices may be used with a wide range of dopants including, but not limited to, substituted phenols, DMMP, methyl salicylate, 2-hydroxyacetophenone, $SO_2$, 2-Chlorobutane. In an embodiment, the dopant to analyte ratio, and particularly in at least a portion of the separation region, is in excess, such as a ratio that is greater than 100 times, greater than $10^4$ times, selected from between the range $10^3$ to $10^{10}$ times, or has a range that is selected from between about $10^4$ and $10^8$ times. A dopant that is present in the system in less than an excess amount may be identified for conditions wherein there are multiple peaks detected by the ion detector of the IMS system. In such a situation, the dopant introduction to the separation region is increased as needed until the additional interfering peaks are sufficiently reduced. Any of the IMS and IMS cells disclosed herein is used to detect an analyte, including for example an analyte in room air, a gas phase sample of analyte, or an analyte transferred to a wipe by a wipe test type method. Depending on the analyte to be detected, and the environment in which the IMS is operating, the drift and/or carrier gas may comprise gas obtained from the environment surrounding the IMS, such as room air. Alternatively, an inert gas or any other gas compatible with transport of analyte and/or dopant is used.

In an aspect, the excess dopant prevents formation of water vapor-generated drift time peaks. Any of the methods provided herein introduce dopant to the separation region by: diffusion from the source of dopant to the separation region; by the flow of a drift gas, or a combination of both.

In an embodiment, the invention is a method of suppressing interference in an ion mobility spectrometer by providing an ion mobility spectrometer having a separation region and an ionization region in fluid communication with each other and introducing a dopant to the separation region at an amount in excess of 0.1 ppm. A sample containing an interfering material and an analyte is introduced to the ionization region and ionized to generate analyte ions. The analyte ions are introduced to the separation region by applying an electric field, such that the dopant provided in excess in the separation region suppresses interference arising from species other than the analyte.

In an aspect, charge transfer from interfering ions in the separation region to the dopant provided in an excess amount suppresses interference from the interfering ions. Any of the methods provided herein are for interfering material that is water, acid, weak acid or strong acid. In an aspect, any of the methods and systems introduce excess dopant to the separation region at a dopant concentration that is selected from a range that is between 0.5 ppm and 500 ppm.

Also provided herein are methods of selectively detecting an analyte by ion mobility spectrometry by providing an ion mobility spectrometer having a separation region and an ionization region in fluid communication with each other. A dopant is introduced to the separation region, wherein the dopant is provided at an amount in excess of 0.1 ppm. A sample containing an analyte is introduced to the ionization region and is ionized to generate analyte ions. An electric field is established in the separation region to introduce the analyte ions to the separation region. The analyte ions are detected based on ion mobility with a detector in fluid communication with the separation region. The dopant provided in excess in the separation region suppresses interference arising from species other than the analyte. In an embodiment, the interference arises from water. In an embodiment, the dopant comprises dimethyl methylphosphonate or methyl salicylate, and the excess dopant amount in the separation region is between 0.5 ppm and 500 ppm.

Without wishing to be bound by any particular theory, there can be discussion herein of beliefs or understandings of underlying principles or mechanisms relating to embodiments of the invention. It is recognized that regardless of the ultimate correctness of any explanation or hypothesis, an embodiment of the invention can nonetheless be operative and useful.

DETAILED DESCRIPTION OF THE INVENTION

Figure 1:
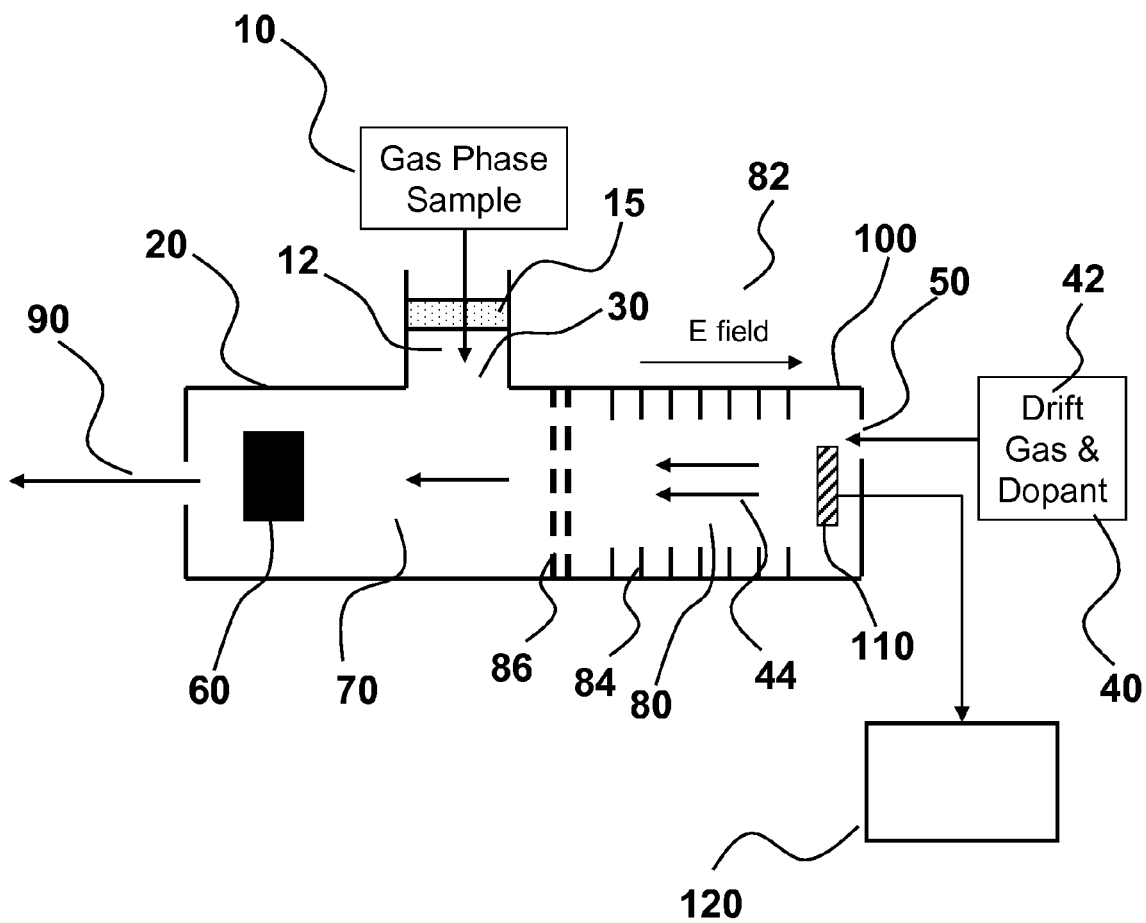
FIG. 1 is a schematic diagram of an IMS cell with improved analyte detection by the introduction of a dopant in the drift gas.

Referring to the drawings, like numerals indicate like elements and the same number appearing in more than one drawing refers to the same element. In addition, hereinafter, the following definitions apply:

"Ion" refers generally to multiply or singly charged atoms, molecules, macromolecules having either positive or negative electric charge and to complexes, aggregates, clusters or fragments of atoms, molecules and macromolecules having either positive or negative electric charge. Ions are generated in the present invention either directly or indirectly from an ionization means, such as a $Ni^{63}$ source.

"Analyte ion" or "detectable ion" refers to ions derived from analyte(s) of interest in a gas phase sample that are capable of separation on the basis of mobility under an applied electric field, and detected in the present IMS methods and systems so as to characterize the identity and/or concentration of the analyte(s) in the sample. Analyte ions are formed in the present invention via one or more processes occurring in an ionization region of an IMS analyzer including direct ionization processes and ion-molecule and ion-ion reactions involving analyte of interest, dopant, dopant ions, and reactant ions generated from the ionization of carrier gas(es), drift gas(es) and/or dopant gas(es). In some embodiments, detectable ions are formed via associative reactions (e.g., adduct formation, cluster formation, etc.) involving analytes and/or ions thereof and dopant(s) and ions thereof. In an embodiment, ion refers to an electrically charged dopant-analyte complex, such as a negatively charged dopant-analyte complex or a positively charged dopant-analyte complex.

"Dopant" refers to compounds that are added to an IMS analyzer to suppress formation of unwanted peaks detected by the IMS. A dopant can be capable of adjusting the flight times of ions. The dopants in the present invention may also be useful for facilitating charge transfer in the separation region and maintaining ion clusters as the clusters travel in the separation region. The IMS systems disclosed herein may be tuned to specifically suppress peaks associated with a variety of compounds. For example, relatively low level of excess dopant in the separation region may be used to suppress water-generated peaks. Increasing dopant levels may be used to suppress weak acids such as $NO_x$-generated peaks, for example. Still higher dopant levels can suppress $SO_2$ and strong acid peaks (HCl, HF, for example) Dopants are useful in embodiments of the present invention for enhancing the sensitivity and selectivity of the present IMS analyzers for detecting, identifying and characterizing analytes in a gas sample. In some embodiments, dopants added to an IMS analyzer selectively adjust the composition and/or flight times of ions, for example, by shifting the flight times of ions such that they are different from the flight times of other ions generated in the analyzer (e.g., reactant ions, dopant ions, ions derived from impurities and interferants such as water vapor). In some embodiments, dopants added to an IMS analyzer selectively adjust the composition and/or flight times of reactant ions, for example by shifting the flight times of reactant ions such that they are different from the flight times of analyte ions. Use of dopants in this aspect of the present invention is useful for generating IMS spectra and detection conditions wherein peaks corresponding to detectable ions separated in the drift region do not significantly overlap with peaks corresponding to other ions generated in the analyzer such as reactant ions, dopant ions, ions derived from impurities and interferants such as water vapor. In certain embodiments, dopant in excess prevents formation of interfering or anomalous peaks. Dopants may be selected depending on the analyte to-be-detected. For example, the dopant may be selected to have a basicity that is between the basicity of the carrier gas and the analyte, for example. Generally, the effect of a particular dopant gas on a given type of ion and ion separation system is difficult to predict a priori, so that selection of a dopant for a given ion involves experimentation that is within the ability of one of skill in the art to select a dopant for a given analyte of interest to maximize instrument sensitivity and reliability. Examples of typical dopants include substituted phenols (for detecting acid gases such as HF, HCl, $Cl_2$, $NO_2$, $SO_2$, carbonyl sulfide, and others), methyl salicylate, 2-hydroxyacetophenone, $SO_2$, 2-Chlorobutane.

"Dopant ions" refer to ions generated from ionization of one or more dopants provided to the ionization region of an IMS. As used herein, dopant ions expressly includes electrically charged monomers, dimers, clusters and complexes of dopants. As used herein, dopant expressly includes electrically charged fragments of dopants, dimers of dopants, trimers of dopants, clusters of dopants and fragments of dopant clusters. In some embodiments, dopant ions refer to negatively charged monomers, dimers, clusters, complexes and/or fragments of a dopant such as methyl salicylate. Dopants and dopants ions of the present invention interact with analyte(s) in a gas phase sample to generate ions that can be analyzed and detected so as to detect, identify and characterized the analyte(s) in the sample.

An ion may be a precursor ion or an intermediate ion that further reacts with other materials. Intermediate ion refers to ions formed from carrier gas(es) and drift gas(es) in an IMS analyzer. In some embodiments, intermediate ions participate in charge transfer reactions resulting in ionization of analytes, dopants or both analytes and dopants, thereby generating ions that are subsequently detected by an ion detector.

"Fluid communication" refers to the configuration of two or more elements such that a fluid (e.g., a gas or a liquid) is capable of flowing from one element to another element. Elements may be in fluid communication via one or more additional elements such as tubes, cells, containment structures, channels, valves, pumps or any combinations of these. For example, an ionization and separation region are said to be in fluid communication if at least a portion of dopant, drift gas and ions are capable of transiting from one region to the other. In certain aspects this fluid communication is one-way (e.g., drift gas traveling from the separation to the ionization region).

"Ion mobility spectrometer" (IMS) is understood in the art to refer to an ionization system used to detect a wide range of analytes on the basis of ion mobility separation. Commonly detected analytes are vapors from substances such as alkaloids, other drugs and controlled substances, explosives, contaminants associated with manufacturing processes including but not limited to chemical processing and refining, semiconductor or pharmaceutical manufacture.

"Analyte" is used broadly to refer to detection of any gas phase substance of interest by IMS, such as for emission, contamination or process control measurements, for example. Such measurement provides environmental assessment, worker protection and process control monitoring and can provide warning when an analyte falls outside a desired concentration range or exceeds an actionable level. Typical IMS analyte measurement applications include, but are not limited to, petrochemical, chemical, refining, waste incineration, power generation, medical and pharmaceutical manufacture, pulp and paper processing, agricultural, water and wastewater treatment and laboratory testing. Accordingly, analyte can generally be an acid gas or a base gas, and more particularly ammonia, chloride, chlorine, HF, HCl, $SO_2$, peroxides, hydrogen peroxide, methyl bromide, chlorine dioxide, acetic acid, for example.

"Carrier gas" refers to a gas that assists in transporting analyte, including analyte in a gas phase sample, to the ionization region. Carrier gas can range from a pure and inert gas such as nitrogen, or to a gas obtained from the environment surrounding the IMS, such as room air. The gas phase sample is optionally itself a room air carrier gas.

"Separation region" refers to the area of the IMS that separates ions based on the effective size of the ion (e.g., collisional cross-section). In an aspect, the separation region comprises a "drift region", such as a drift tube region wherein drift gas flows in a direction opposite to the E field-induced movement of the ions.

A dopant in "excess" refers to providing dopant to the system sufficient to dominate or drive cluster formation and/or provide charge transfer with ions in the separation region. Typically, excess dopant is measured as the number of dopant ions and un-ionized dopant in the separation or drift tube region. The specific amount of dopant required in order for a system to be considered to have "excess dopant" depends on a number of factors. One factor is the composition of the gas phase sample, and in particular amount and type of interferent(s) and/or analyte(s). Another factor involves the separation region characteristics such as wall effects (e.g., dopant/wall interaction). Dopant is added in sufficient quantity to rapidly obtain steady state equilibrium with the wall, thereby ensuring high concentration of dopant in the drift region to assist in driving chemical kinetics toward dopant-dominated chemistry, such as dopant dimerization and dopant-analyte clusters. This excess ensures rapid instrument response time, maximizes peaks that are used for analyte detection and minimizes unwanted peaks that are not required for analyte detection and that could, in fact, hinder analyte detection. In addition, dopant levels are varied depending on the charge transfer reactions of interest in the separation region, including the species responsible for the peak that is desirably suppressed. In general, less dopant is required to suppress water and, in order of ascending dopant level, weak acids (e.g., NO, $NO_2$), $SO_2$, and strong acids. Accordingly, parameters of interest for selectively tuning the IMS to suppress unwanted peaks include charge affinity of the interfering substance and/or the dopant as well as the concentration level of the dopant in the separation region.

Dopant is provided to the IMS system, and more particularly, to the separation region by any means known in the art. For example, U.S. Pat. No. 5,491,337 discloses adding dopant molecules to a carrier gas stream. In a similar fashion, dopant molecules can be mixed directly with the drift gas stream prior to introduction to the separation region to provide high concentration dopant. "Drift gas" refers to the gas that flows in a direction opposite to E field-induced ion mobility. The drift gas may itself be the dopant, for example a dopant suspended in an inert gas, such as nitrogen gas. A drift gas is said to flow in a direction that is "substantially opposite" to the electric field in the separation region if the average directions of the field and flow are within 10% of each other.

"Substantially" also refers to the fraction of analyte or water vapor in a gas phase sample that is introduced to the ionization region. In an embodiment, "substantially all" refers to at least about 50%, 70%, 90%, between 75% and 95%, or about 100% of the analyte in the sample being introduced to the ionization region. IMS systems having membranes typically only supply about 35% of gas phase analyte to the ionization region, as a significant fraction is excluded by the membrane. The amount of water vapor that is excluded similarly depends on the properties of the hydrophobic membrane.

Dopant is "substantially constant" in a system when the local dopant concentration varies less than about 10%, 5%, or 1% than the region-averaged dopant concentration over the entire region.

"Ionization source" refers to a component capable of ionizing gaseous material positioned in the ionizing region. As known in the art, this source can be a radioactive source of β-particle ionizing radiation such as $Ni^{63}$ or another ion-generating means such as corona discharge or electrospray.

"Pulsed flow" refers to introduction of sample to the IMS system in a periodic manner. Any desired periodicity may be provided, such as on the order of minutes or hours, for example.

"Suppressing interference" refers to measurably decreasing a peak generated by an interfering compound as detected by the spectra output from the IMS system. This decrease may be expressed as a reduction in the amplitude of the peak, such as reduction of 25%, 50%, 75% or more. Alternatively, as this suppression makes available charge for analyte ion clusters useful in detecting analyte, the suppression may be correspondingly expressed as an increase in a peak of interest, such as increasing a peak of interest by 25%, 50% or 75% or more. Similarly, the suppression may be expressed as a ratio between a peak of interest and an interfering peak (see FIGS. 3-8).

"Selectively detecting" an analyte refers to providing excess dopant in the separation region to provide improved overall detection of an analyte, such as by reducing peaks associated with interfering ions (such as water) detected by the IMS and/or increasing the detected peaks arising from the analyte of interest.

The general configuration of an ion mobility spectrometer (IMS) is known in the art (see, e.g., U.S. Pat. No. 5,095,206). In IMS, gas phase ion mobilities are determined using a separation region having an electric field to separate ions based on their differences in drift velocity. At low electric field strengths, the drift velocity of an ion is proportional to the applied electric field strength. In general, a drift gas that flows in a direction opposite to the ion drift velocity direction facilitates relatively rapid attainment of a constant ion velocity.

One strategy for introducing gas phase samples and dopant in an IMS system is schematically illustrated in FIG. 1. As provided in FIG. 1, gas phase sample 10 potentially containing an analyte is introduced to an ion mobility cell 20 at inlet 30. Optionally, a membrane 15 is positioned upstream of the cell 20 (e.g., upstream of inlet 30) for removing unwanted contaminants within the gas phase sample. In an embodiment, transport of gas phase sample is facilitated by flow of carrier gas 12. Carrier gas 12 is optionally introduced at least in part by a flow conduit that is separate from gas phase sample. The gas phase sample 10 is introduced to the act ionization region 70 having an ionization source 60 for generating ions. Ions are driven to ion detector 110 by an electrostatic field 82 generated by electrodes 84 positioned in separation region 80. Shutter electrode 86 facilitates entry of ions into separation region 80 from ionization region 70. Ions are detected by ion detector 110 and related data acquisition and processing unit 120. Selective activation of shutter 86 permits selective ion build-up in ionization region 70. In an embodiment, the system is run in enhanced mode as outlined in U.S. Pat. No. 4,950,893, where the function of the shutter grid is reversed (e.g., shutter normally biased open and briefly biased closed). In an embodiment, the system is run in normal mode (e.g., shutter normally biased closed and briefly biased open).

Dopant 40 is introduced to cell 20 at dopant inlet 50. The dopant may itself be the drift gas 42 that travels in a counter-current direction as indicated by arrows 44 relative to the direction of ion travel under applied E field 82 in separation region 80. Dopant inlet is positioned to permit introduction of dopant directly to separation region 80. In general, drift flow 44 (indicated by the arrows) is generated by flow of dopant 40 and drift gas 42 from a reservoir or a dopant-containing reservoir and separate source of drift gas through separation region inner walls 100, and traverses separation region 80 and ionization region 70 and removed from cell 20 at an exhaust port 90. The relative positions of dopant inlet 50, gas inlet 30, and exhaust outlet 90 are capable of any number of geometries, configurations and relative positioning. In an embodiment, drift flow in drift flow 44 is in a direction that is opposite the direction of the drift velocity of ions along E field 82. In an aspect, separation region 80 comprises a drift tube.

Figure 2:
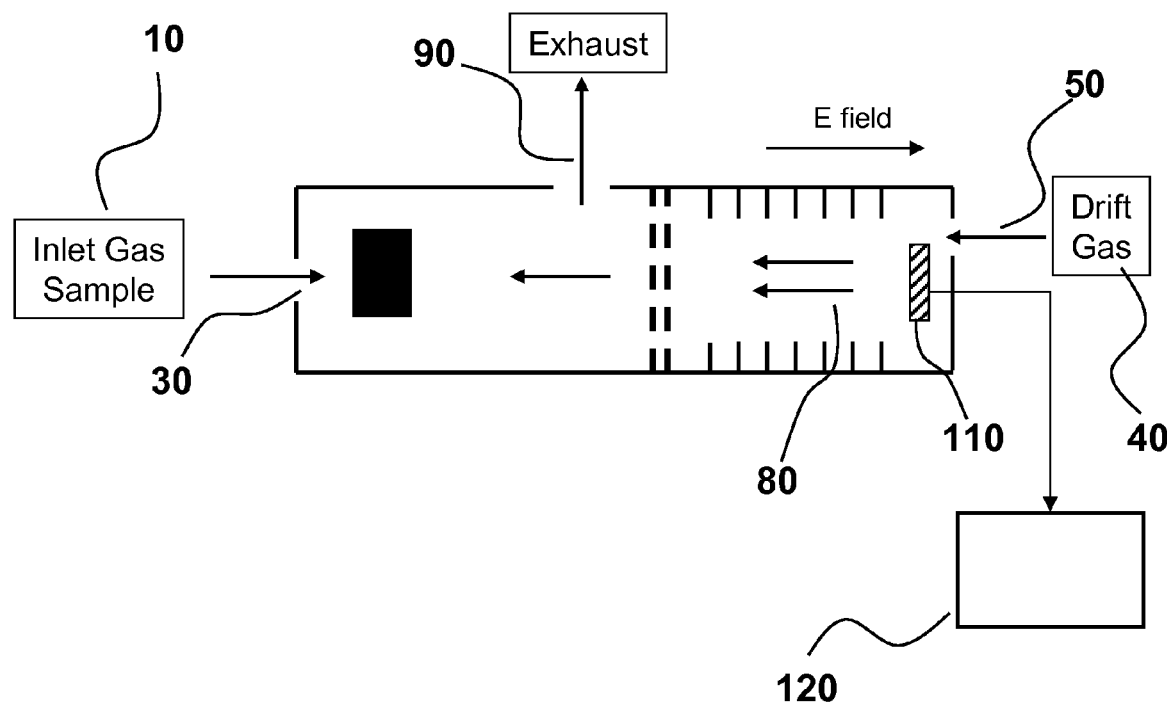
FIG. 2 is a schematic diagram of an IMS cell similar to that shown in FIG. 1 with a different sample gas inlet and exhaust configuration.

Another example with a modified relative port positions is provided in FIG. 2. In this example, the inlet 30 and exhaust 90 locations are switched. FIG. 2 illustrates that membrane 15 is not required for sensitive and reliable analyte detection, even in the presence of potentially interfering substances in the sample because of the addition of dopant to the separation region in an excess amount. In the two systems depicted in FIGS. 1-2, the dopant and drift gas is shown as introduced together at one end of the IMS cell 20. Alternatively, the dopant may be added separately to the separation region 80 and be subsequently dispersed and carried throughout the IMS cell 20 by drift gas.

Features of ion mobility spectrometers known in the art, such as power supply, shutter grid, aperture grid, flow regulators, gas sources and flow conduits for conveying drift gas, carrier gas, sample gas to the cell, diffusers, sample chambers, scrubbers, permeation tubes, ionization chamber, grid electrodes, field-defining electrodes, signal processing components such as amplifiers and data processors, and/or temperature control, are incorporated as needed. The applied electric field that drives ions toward the collector electrode or ion detector 110 may be applied periodically to permit ion build-up and subsequent sweeping of ions into the drift gas region. Typical electric fields range on the order of 100 s V/cm, e.g., about 600 V/cm or less than about 600 V/cm for gases in the IMS cell at atmospheric pressure, including about 150-180 V/cm.

Figure 3:
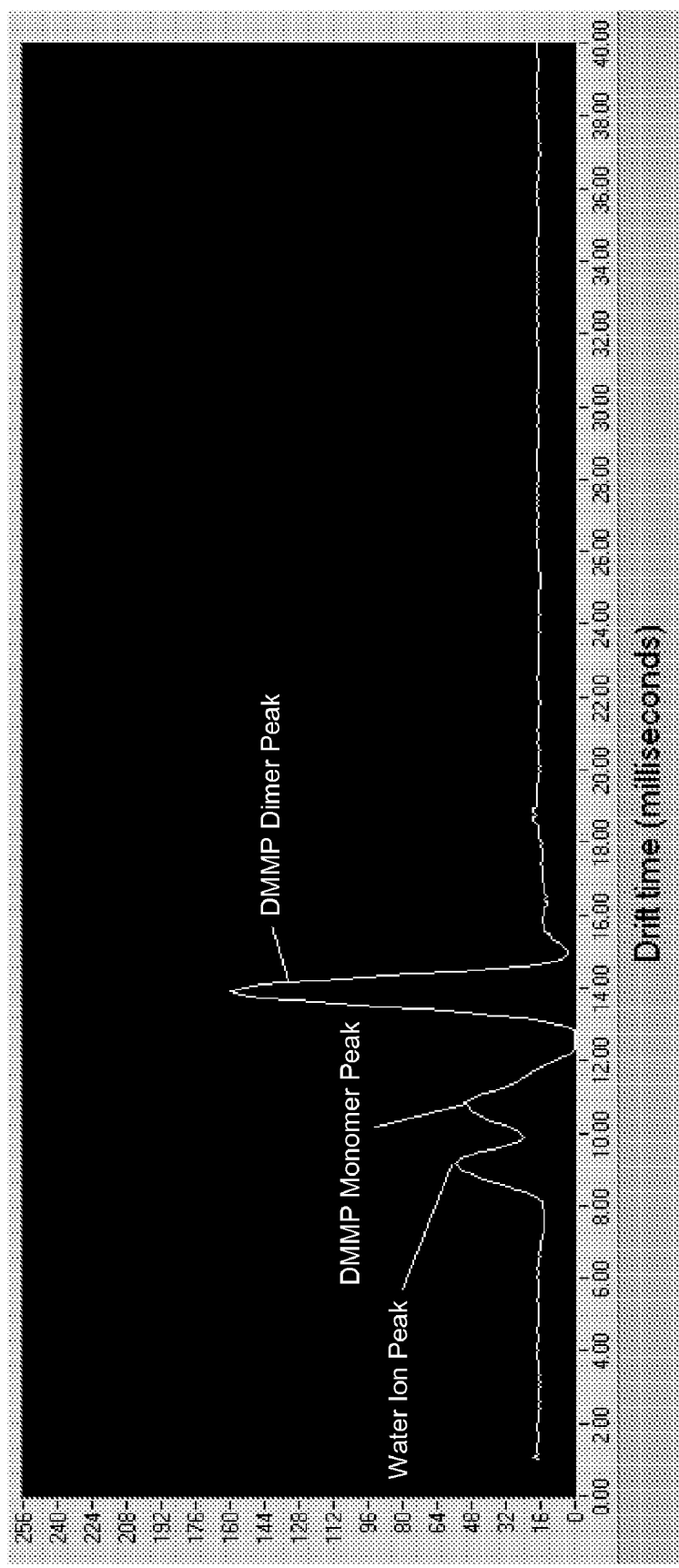
FIG. 3 is a graph showing drift time in an ammonia analyzer with DMMP dopant (about 2 ppm DMMP) introduced at the ionization region with the sample gas (corresponding to low ppt dopant in the separation region). No ammonia is contained in the sample. Three distinct peaks are observed.
Figure 4:
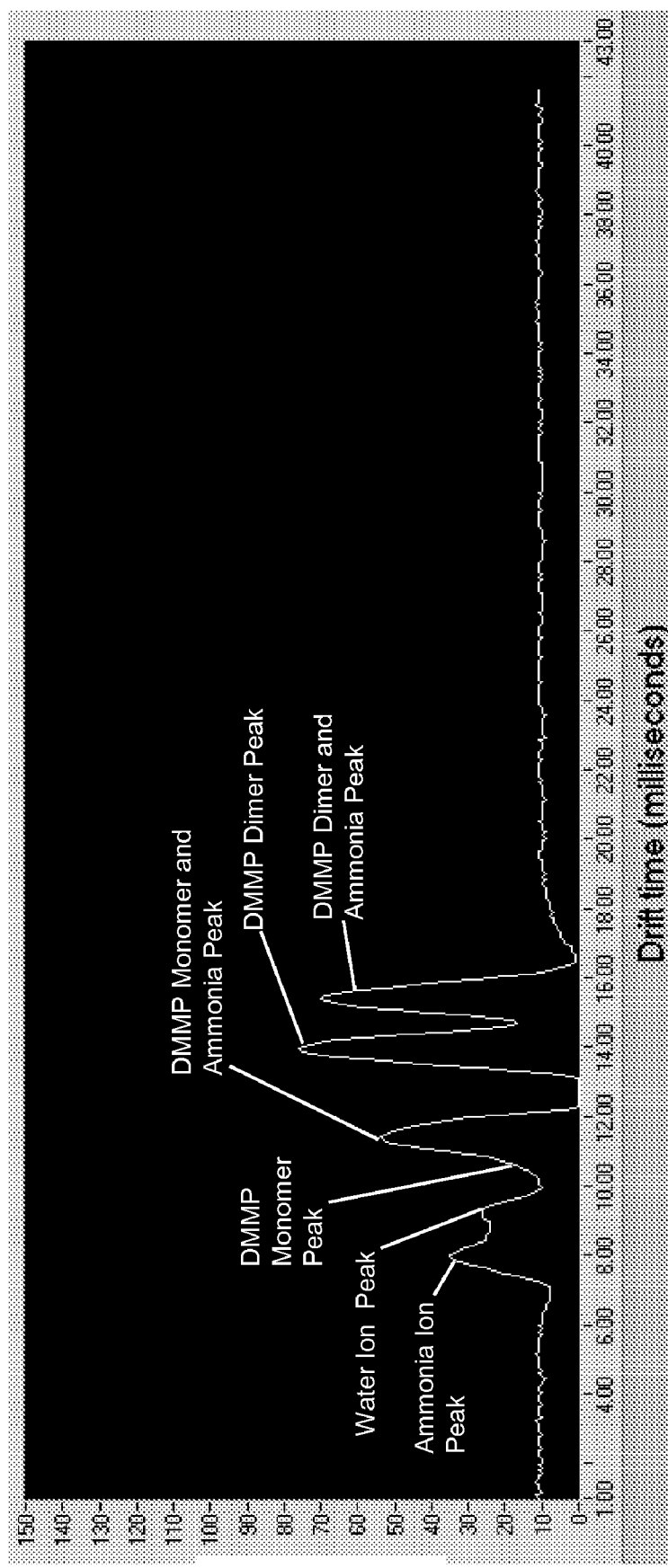
FIG. 4 is a graph showing drift time in the ammonia analyzer of FIG. 3 with DMMP dopant (about 2 ppm DMMP) introduced at the ionization region, for sample gas containing 50 ppb ammonia (corresponding to low ppt dopant in the separation region). As labeled, the IMS detects six distinct peaks in the ion signature: $NH_4(H_2O)$, $H_2O$, DMMP monomer, DMMP monomer+$NH_4$, DMMP dimer, and DMMP dimer+$NH_4$.

FIGS. 3-6 provide examples of spectra obtained by different IMS analyzer systems. The analyzer in FIGS. 3-4 is configured for dopant addition to the ionization region, whereas the analyzer in FIGS. 5-6 adds dopant to the separation region. In both systems, the dopant is DMMP and the analyte is ammonia.

Referring now to FIGS. 3 and 4, potentially interfering peaks are detected by the IMS system in the presence of no analyte (FIG. 3) and in the presence of 50 ppb ammonia (FIG. 4). Even without the addition of analyte, FIG. 3 indicates that three peaks are observed that are associated (from left-to-right, respectively) with a water ion peak, a DMMP monomer peak, and a DMMP dimer peak. The problem presented with unwanted detection of contaminant peaks is illustrated in FIG. 4, where multiple peaks not used in analyte detection are detected. In this system, the peaks (from left to right, respectively) are: ammonia ion, water ion, DMMP monomer, DMMP monomer and ammonia, DMMP dimer, and DMMP dimer and ammonia. Ammonia detection, in this system, only uses two peaks (DMMP dimer and DMMP dimer+ammonia peaks; e.g., the two right-most peaks) to calculate ammonia concentration. The other four peaks consume charge, but do not provide any utility in terms of calculating analyte concentration in that IMS system. FIGS. 3-4 illustrate that almost half of the ions formed and detected by the ion detector are not available for use in detecting analyte (e.g., ammonia). FIGS. 3 and 4 have a carrier gas, sample gas, and drift gas flowrate of 135 mL/min, 500 mL/min and 135 mL/min, respectively. Because dopant is not added directly to the separation region, the dopant concentration in the separation region is low, on the order of ppt or less. The system is run at 50° C. at ambient pressure.

Figure 5:
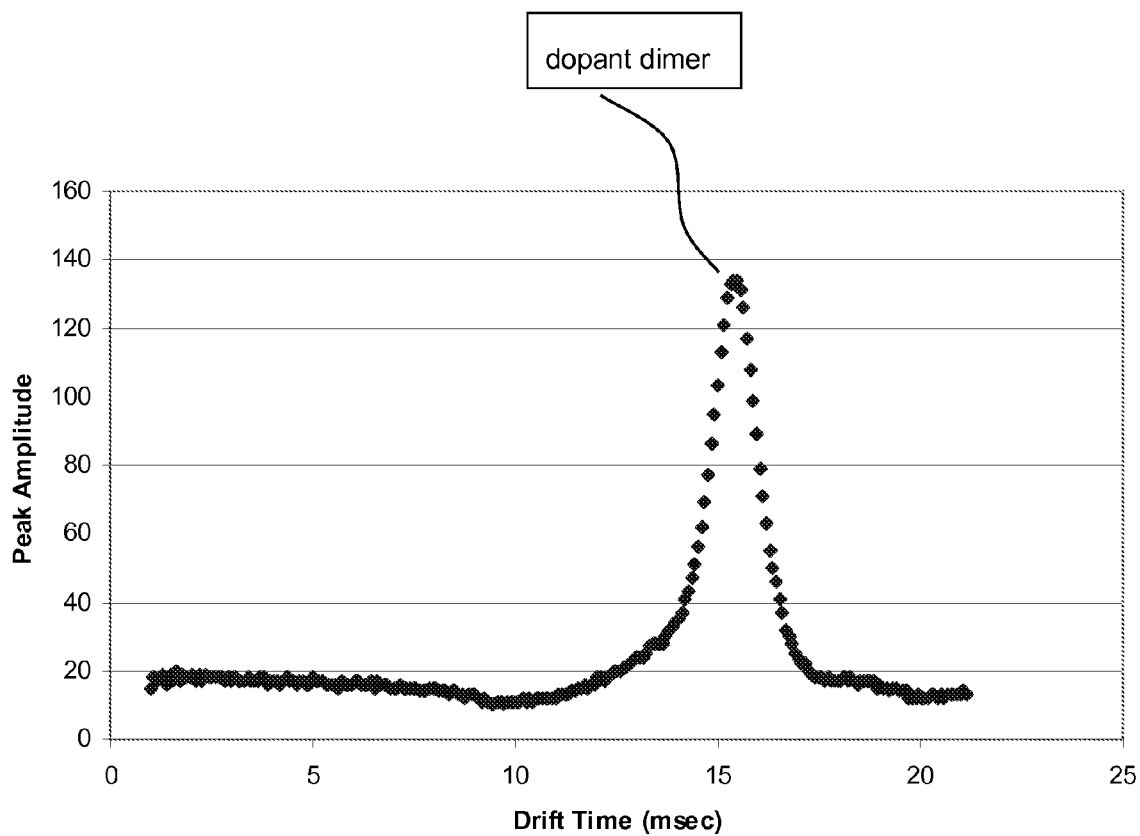
FIG. 5 is a graph showing drift time in an ammonia analyzer with DMMP dopant introduced in excess (about 1 ppm DMMP) to the separation region. The sample gas contains no ammonia. In contrast to the three peaks detected in FIG. 3, only a single peak is observed corresponding to dopant dimer clusters.
Figure 6:
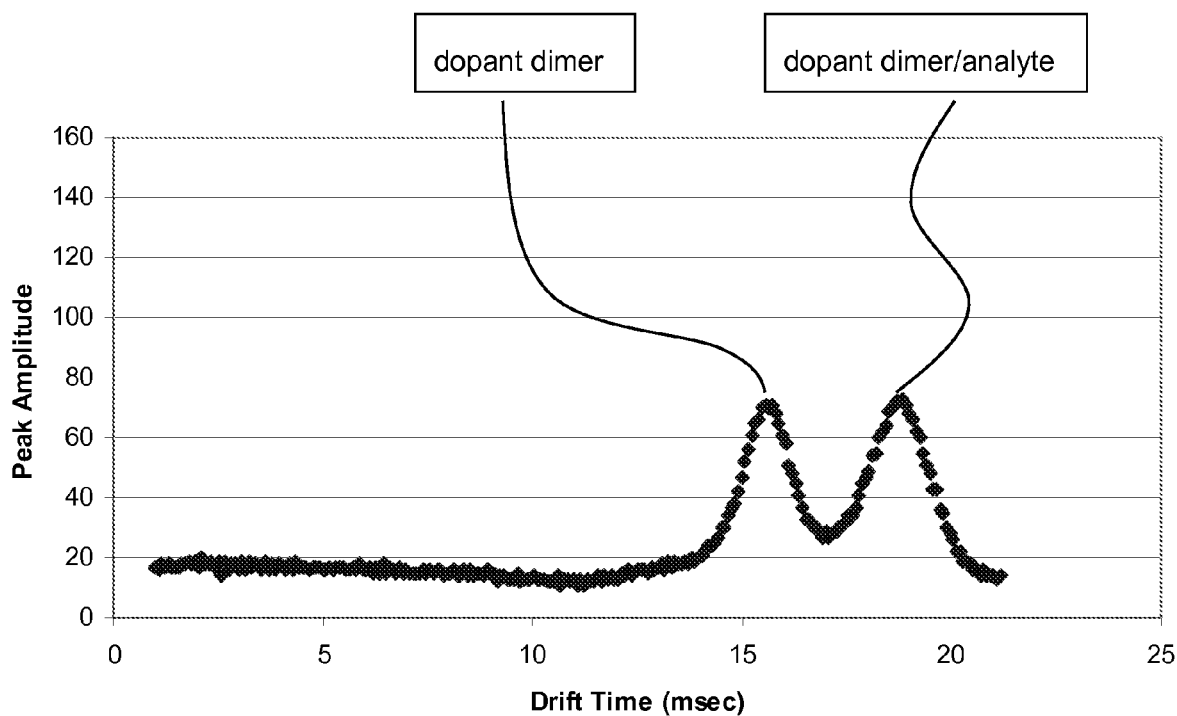
FIG. 6 is a graph showing drift time in the ammonia analyzer of FIG. 5 with 25 ppb ammonia gas and about 1 ppm DMMP introduced to the separation region. In contrast to the six peaks detected in FIG. 4, only two peaks are observed corresponding to the two peaks used for detection of the analyte of interest (e.g., dopant dimer peak and dopant dimer/analyte cluster peak).

Data obtained from a system that introduces high concentration of dopant to the separation region is provided in FIGS. 5-6. Comparing FIGS. 5-6 to FIGS. 3-4, respectively, one notices the dramatic reduction in total number of peaks such that in the analyte-free system (FIG. 5), only a single dopant dimer peak is observed. The dopant monomer and water ion peak do not form because of the presence of excess dopant in the separation region. Similarly, when analyte is introduced to the system (25 ppb ammonia, see FIG. 6), the presence of high concentration of dopant in the separation region prevents formation of peaks associated with water, so that only two peaks remain, the dopant dimer and the dopant dimer/analyte. Those are the two peaks used for detection. The water peak does not form under these conditions, even when no membrane is used. Accordingly, a configuration that introduces excess dopant to the separation region provides methods and systems having improved sensitivity and stability, while reducing interference from unwanted contaminants introduced to the system including, but not limited to, water vapor. In any of the methods and devices disclosed herein, a membrane is optionally not used. In FIGS. 5 and 6 there is no carrier gas and the sample gas and drift gas flowrate is 460 mL/min and 90 mL/min, respectively. The dopant concentration in the separation region is about on the order of 1 ppm, and the system run at 50° C. at ambient pressure.

Figure 7:
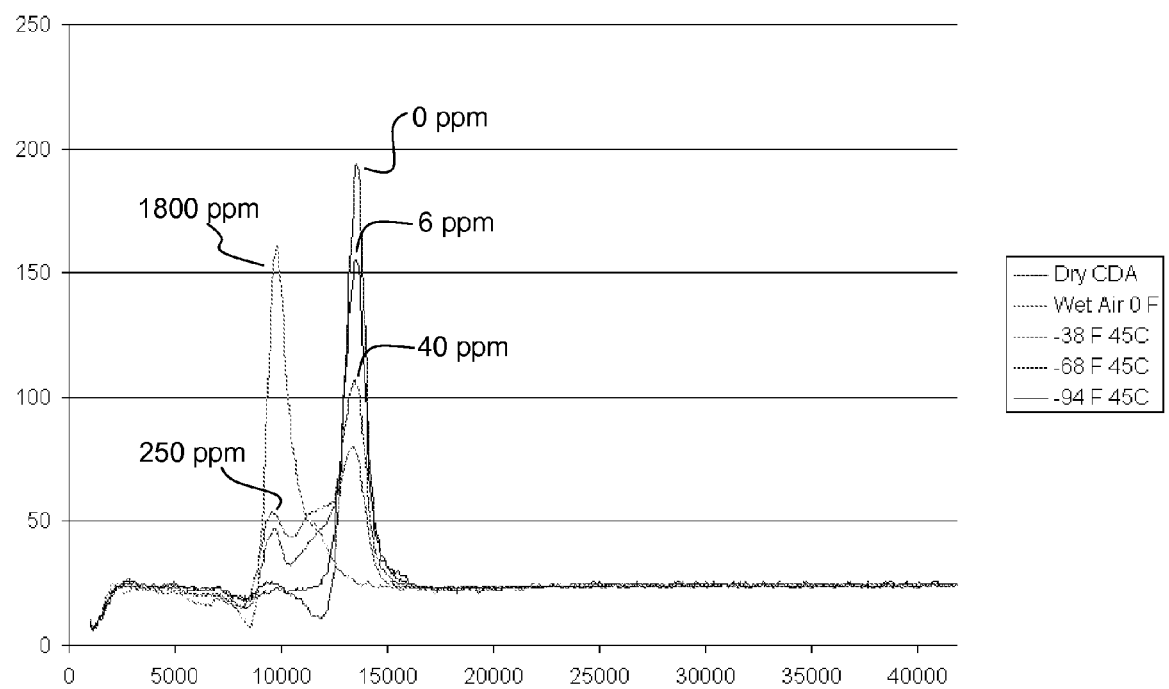
FIG. 7 is the detected spectrum of an IMS system having 100 ppm of methyl salicylate (MS) dopant for 5 different samples each having different concentration of water (0, 6 ppm, 40 ppm, 250 ppm, 1800 ppm) as indicated.
Figure 8:
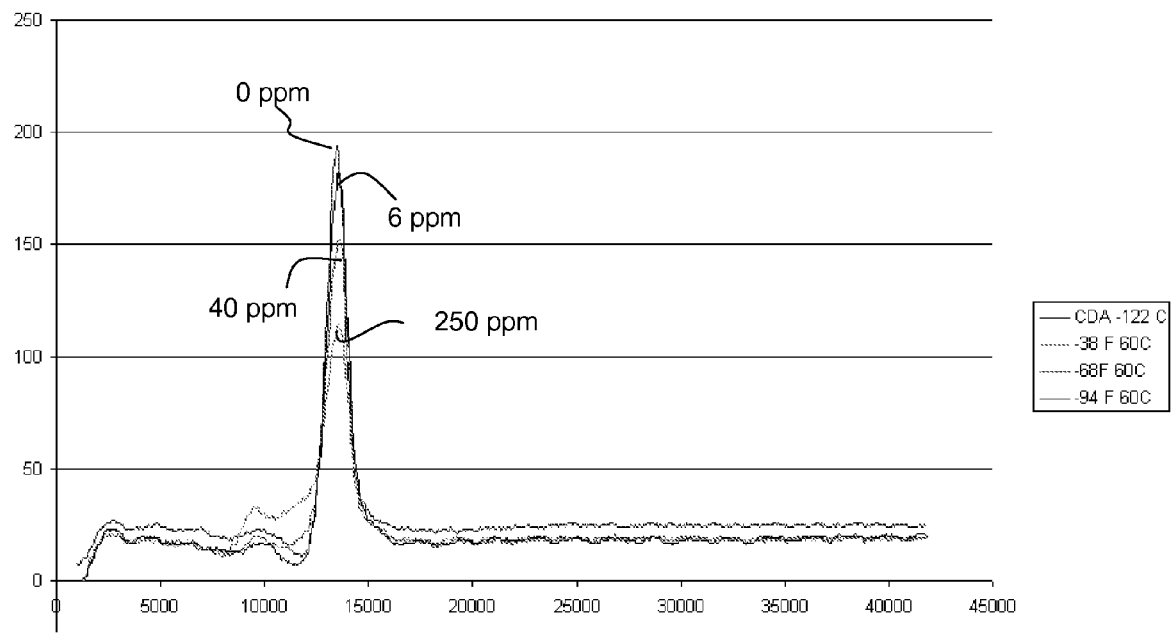
FIG. 8 is similar to FIG. 7 except the MS dopant is about 350 ppm. These data show the higher dopant level in the separation region significantly suppresses the water-generated peak.

FIGS. 7 and 8 illustrate the benefit of increasing dopant concentration in the separation region to suppress unwanted and potentially interfering peaks detected by the IMS. In the exemplified system the effect of MS dopant on water-induced peak generation is examined. The difference between the systems associated with FIGS. 7 and 8 is the amount of dopant introduced to the separation region (100 ppm versus 350 ppm). For both experiments, spectra are obtained for different water levels ranging from 0 to 1800 ppm in FIG. 7 and 0 to 250 ppm in FIG. 8. FIG. 7 illustrates the location of the water peak is to the left of the peak associated with the dopant (compare 1800 ppm and 0 ppm spectra). Increasing the dopant concentration in the separation region from 100 ppm to about 350 ppm results in a significant suppression of the water-associated peak (see FIG. 8 and compare water peak for 250 ppm water with that in FIG. 7). In a similar manner, any one or more interfering peaks associated with other substances may be suppressed by manipulating the dopant concentration in the separation region.

Figure 9:
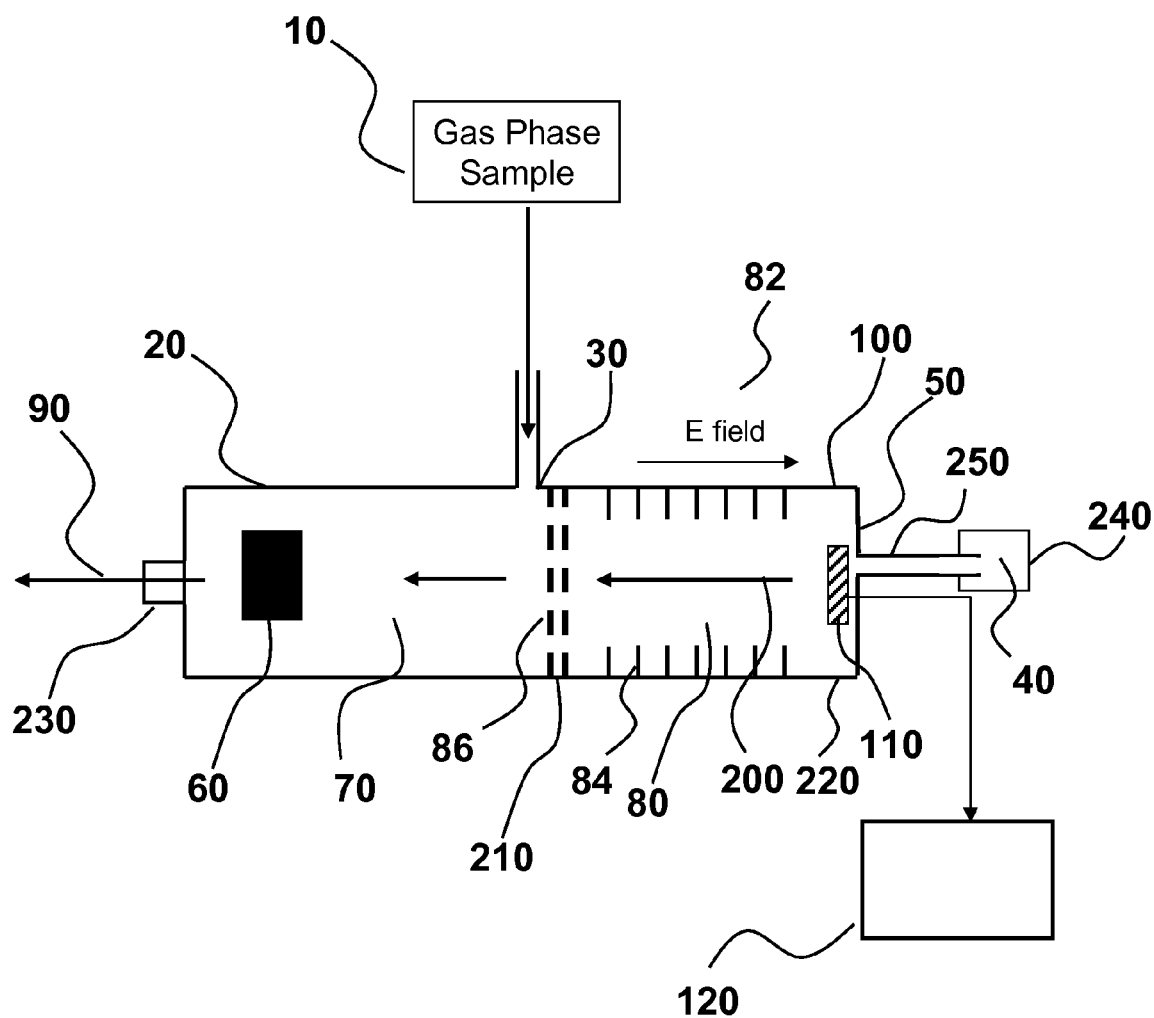
FIG. 9 is a schematic diagram of an IMS cell with improved analyte detection by the introduction of a dopant by diffusion without drift gas to generate a dopant having a significant concentration gradient within the separation region.
Figure 10:
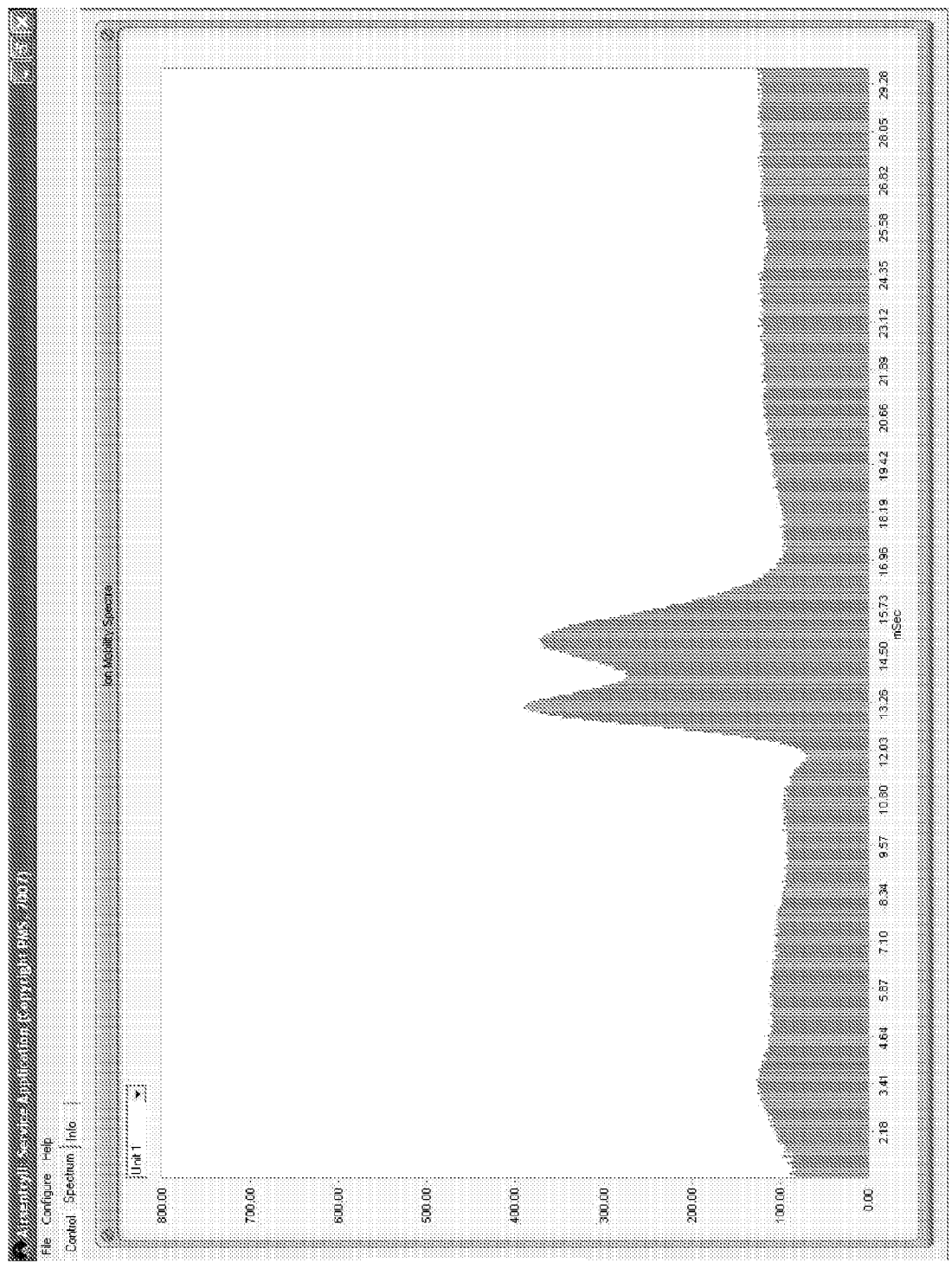
FIG. 10 is the detected spectrum from a high sensitivity ammonia analyzer for 5 ppb ammonia. The analyzer is operated without drift gas. The dopant is introduced to the separation region by diffusion.
Figure 11:
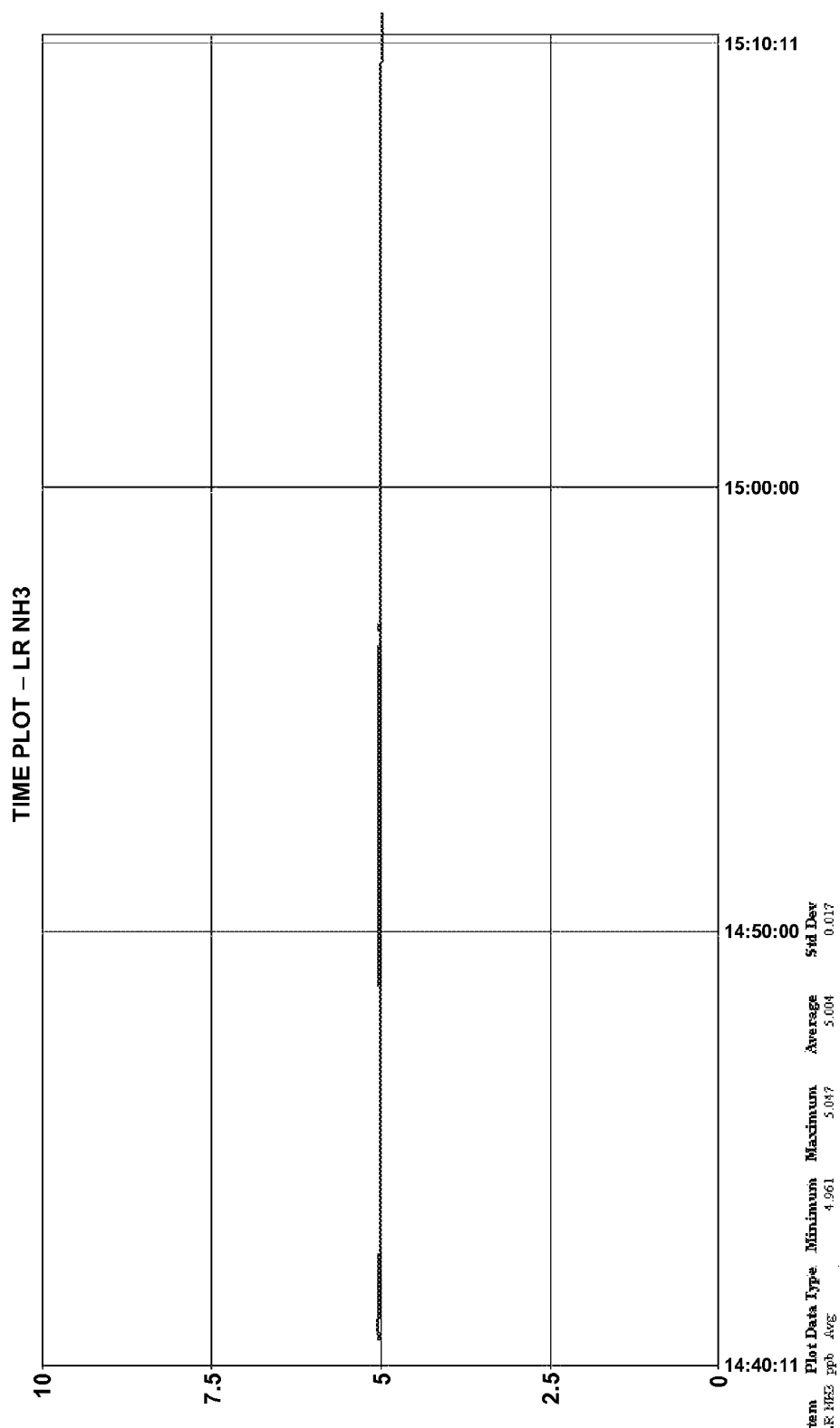
FIG. 11 shows span gas stability with 5 ppb humidified ammonia. The IMS analyzer is operated in the configuration depicted in FIG. 9
Figure 12:
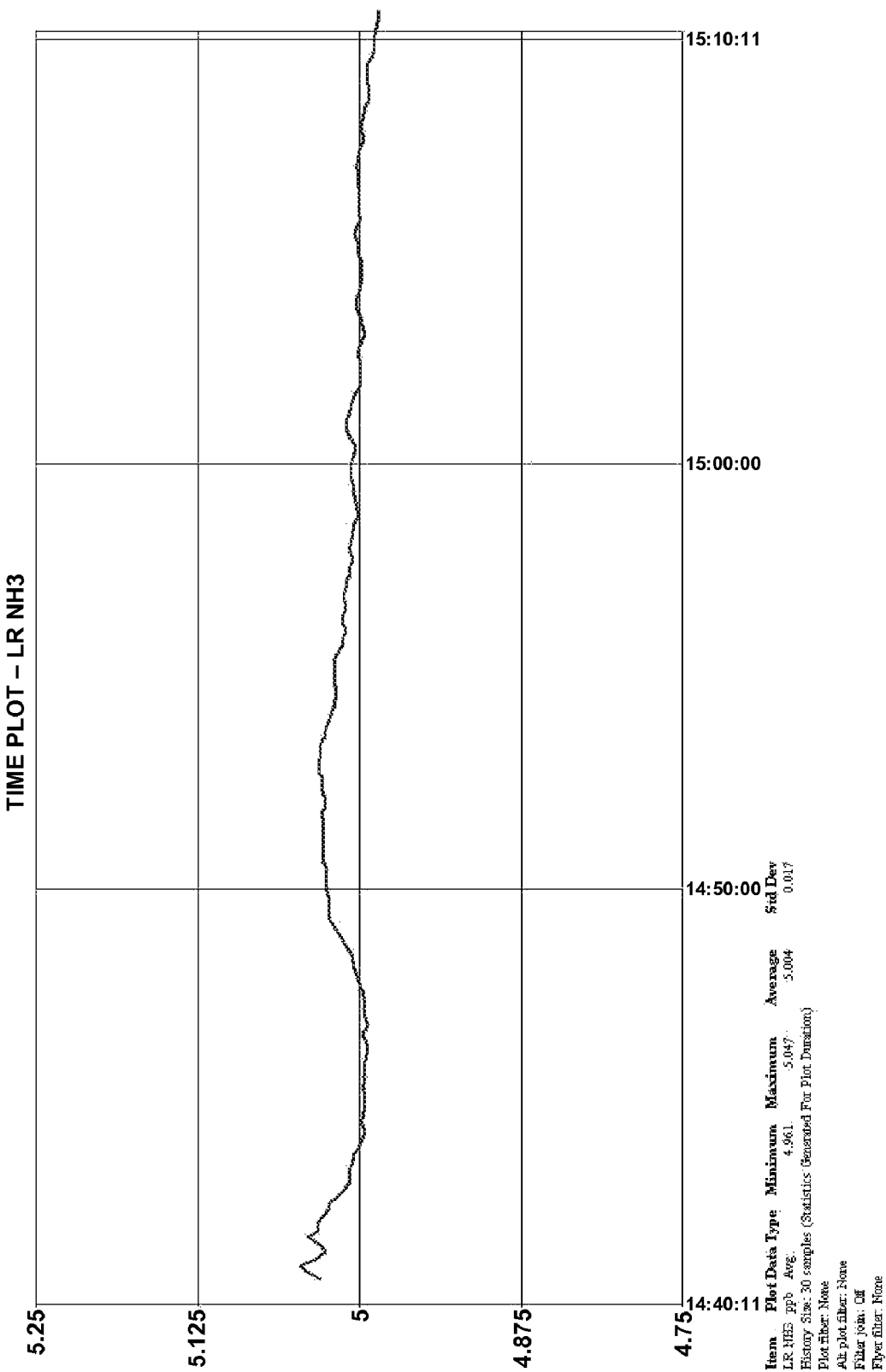
FIG. 12 shows the measurement stability of a 5 ppb ammonia span gas sample at a 500 ppt plot scale (sigma=17 ppt).
Figure 13:
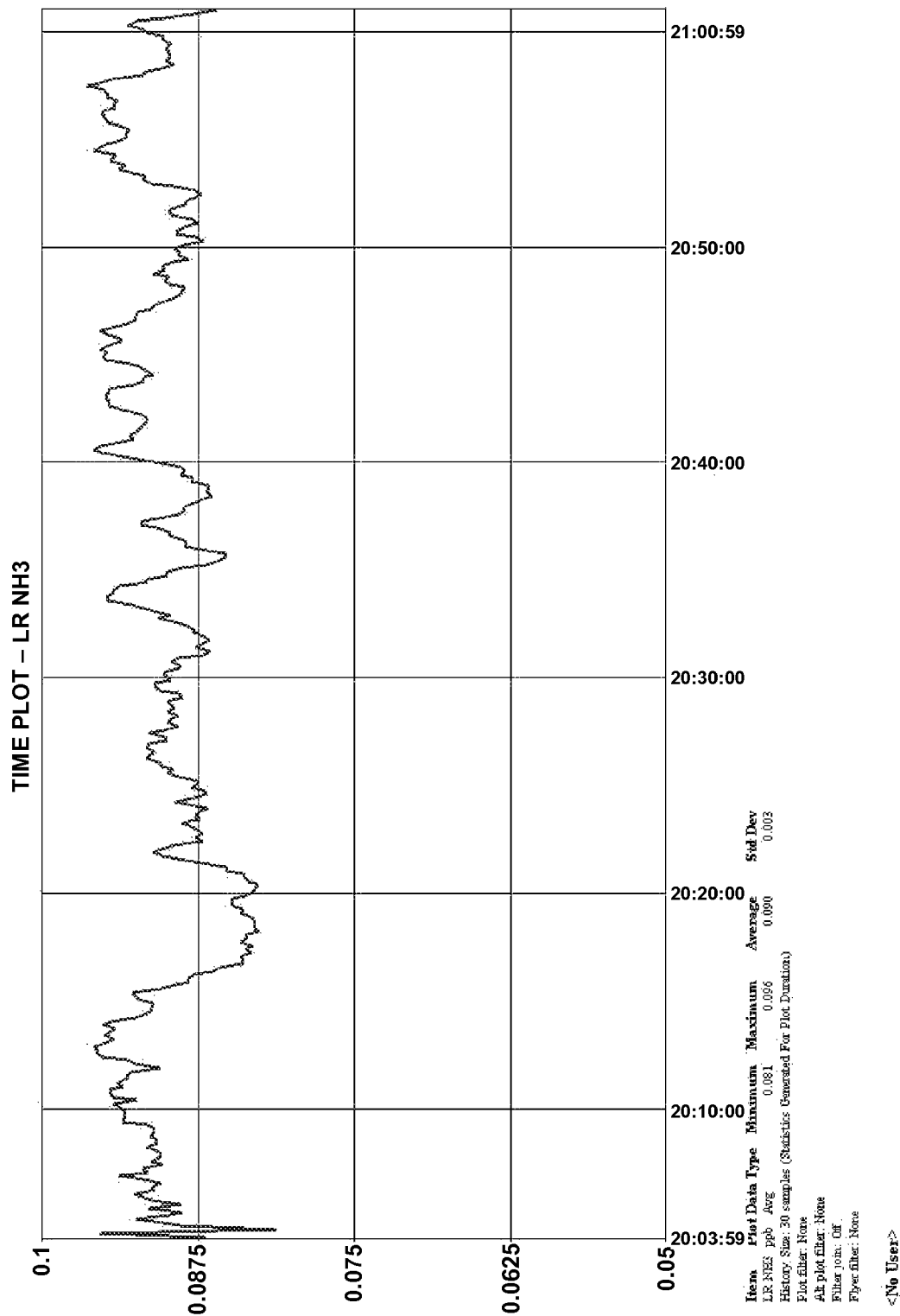
FIG. 13 is a one hour zero stability plot (500 ppt plot scale; sigma=3 ppt).
Figure 14:
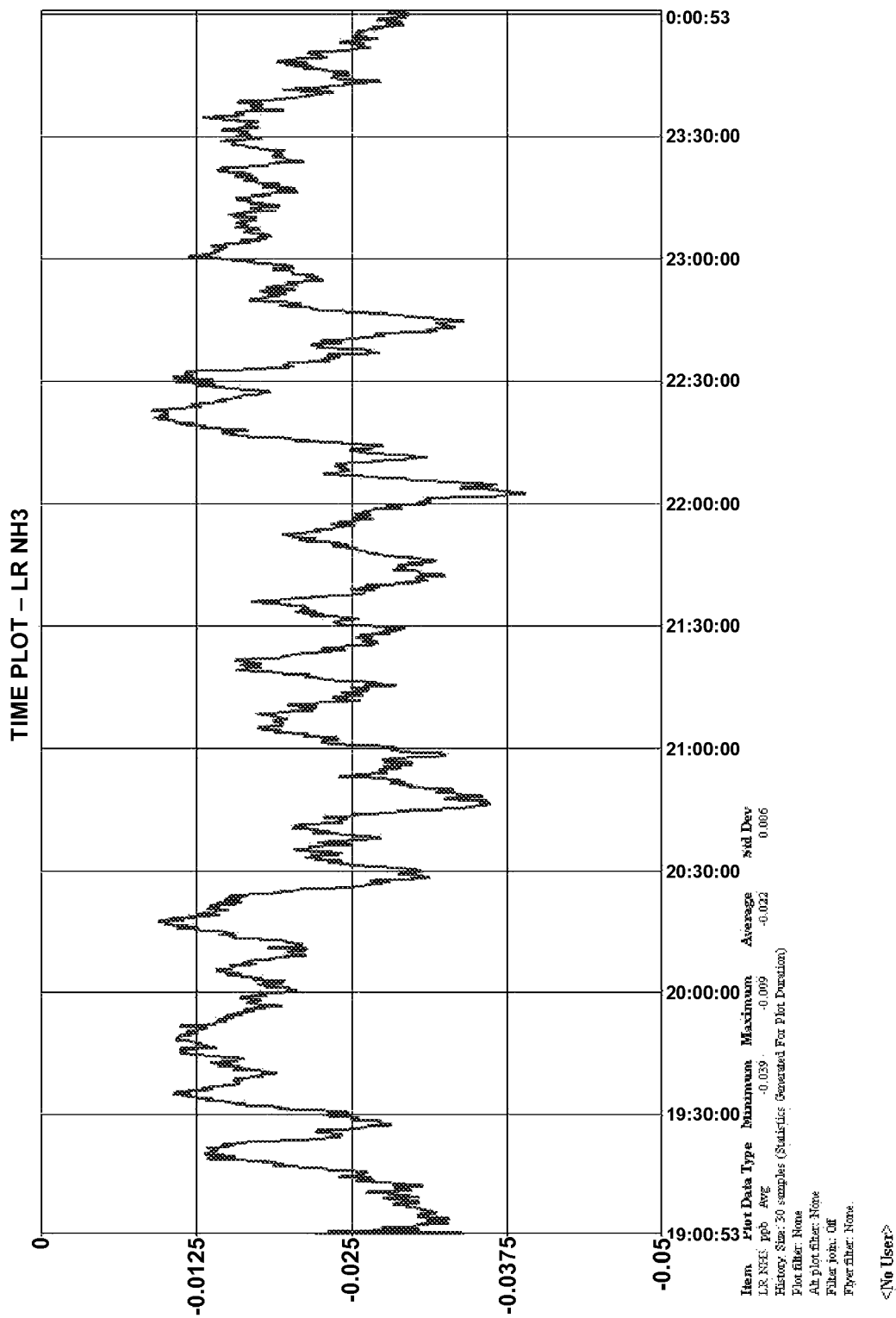
FIG. 14 is a 5 hour plot of zero stability (50 ppt plot scale; sigma=64 ppt)
Figure 15:
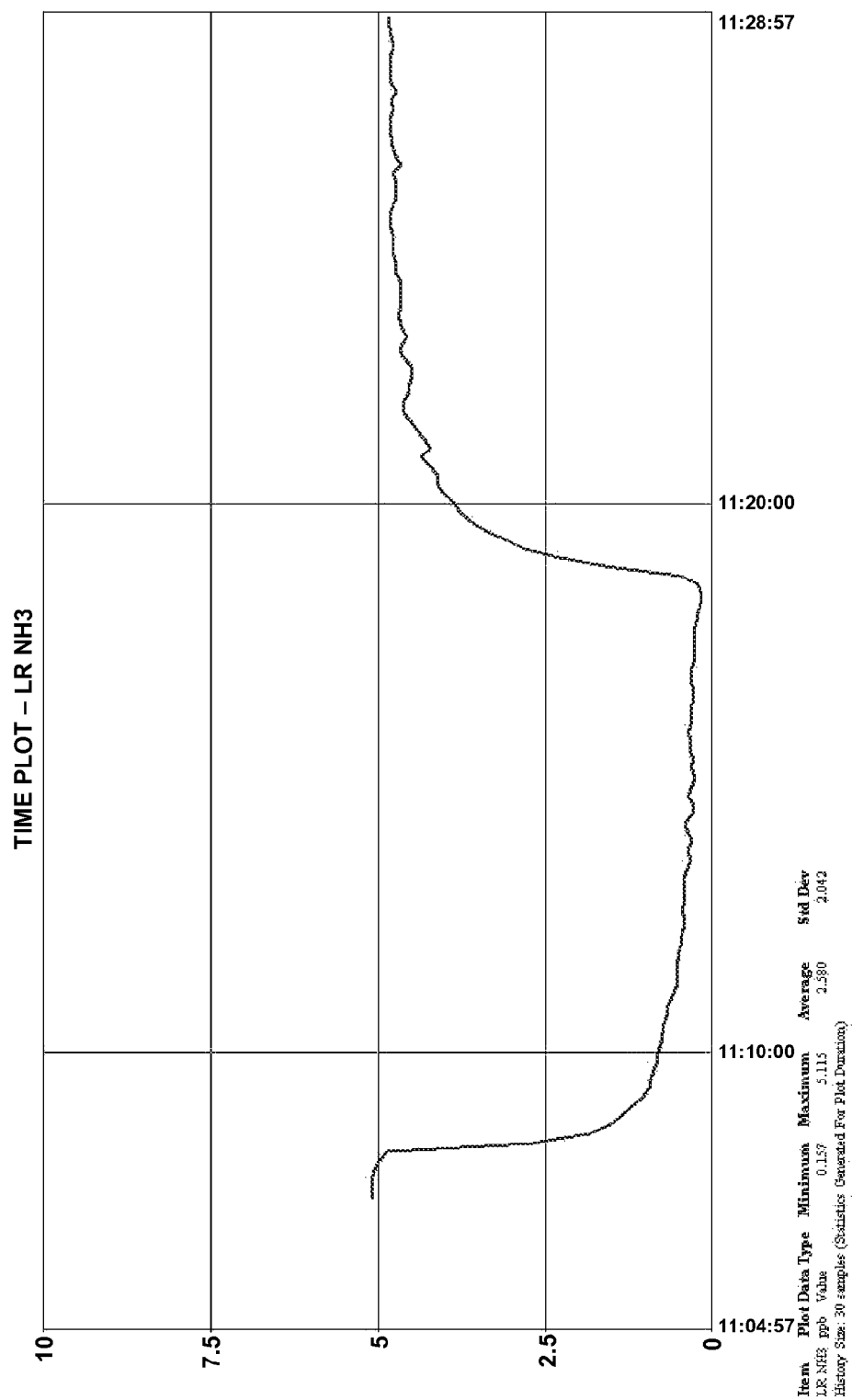
FIG. 15 shows the IMS analyzer's response to 5 ppb of ammonia and response to zero air (3 min 90%; 10 min 95% and 4 min 90%; 10 min 95%).

IMS using a dopant concentration gradient in the separation region: Introducing a concentration gradient of dopant in the separation region facilitates access to low-level analyte detection. In this embodiment, the dopant 40 is introduced to the ion collector or detector 110 end of the separation region 80 by diffusion, as schematically illustrated in FIG. 9. Dopant 40 is introduced to a second end 220 of separation region 80 corresponding to the end near ion detector 110. Dopant 40 is positioned in holder 240 that is introduced to separation region second end 220 by conduit 250. The length, geometry and size of conduit 250 is adjusted as needed (e.g., lengthened/shortened; widened/narrowed) to provide a desired dopant concentration at a particular location or overall dopant concentration gradient in separation region 80. Such introduction of dopant to the second end 220 establishes a concentration gradient of dopant in the cell, wherein there is a flux of dopant along the longitudinal direction (as indicated by the arrow 200) of the separation region 80 by diffusion. No bulk air flow or drift gas to convey the dopant from the dopant source to the IMS cell is required. The air sample 10 is introduced at an inlet 30 positioned near or at the shutter grid 86 (e.g., a volumetric flow-rate on the order of a few hundred ml/min) and is exhausted from the ionization region 70 at the end of the cell 90. In this configuration, the dopant 40 has a concentration gradient in the cell, such as a dopant concentration that is very low at the first end 210 of separation region 80 corresponding to shutter grid 86 and in the ionization region 70 of the IMS cell. The dopant concentration is at a maximum value at the ion collector 110 and second end 220. A large concentration gradient exists across the drift tube and separation region of the IMS cell. Flow of air sample 10 ensures analyte and dopant are well-mixed at the shutter grid 86 and first end 210 and maintains a low dopant concentration at the separation region first end 210.

Depending on the operating conditions (e.g., analyte amount, level of interfering material) the flow rate of air sample 10 is adjusted by a flow rate control 230. In this example, flow rate control 230 corresponds to a source of vacuum connected to the exhaust of the IMS, as indicated by the arrow of exhaust flow 90. Exhaust flow 90 is controlled by using an orifice or needle value. Accordingly, the air sample flow containing analyte equals exhaust flow rate minus drift flow. In this example, there is no need for an orifice or valve in the introduced air sample stream, thereby avoiding problems associated with alterations in the composition of the air sample. In this context, however, "adjustable flow-rate control" is used broadly to include any devices known in the art to controllably affect flow-rate, including but not limited to, positive pressure devices such as forced-air blowers, motors, pumps and/or negative pressure devices such as vacuum sources, so long as the flow-rate control is capable of controlling the flow-rate of the introduced air sample. "Operably connected" refers to a configuration of the flow-rate control and the inflow of air sample of the present invention such that functionality of the control is preserved when connected. Operably connected refers to an arrangement wherein manipulation of the flow-rate control is transmitted to air sample inflow. Accordingly, the flow-rate control need not be directly in the path of air sample inflow, but instead is optionally positioned in a functionally convenient location such as corresponding to the exhaust port.

The concentration of dopant relative to the concentration of the analyte at the ion shutter location determines the responsivity of the IMS system. Because of charge sharing between the dopant and target, if the dopant concentration is reduced at the shutter grid, the target ion peak will increase, resulting in higher analyte sensitivity. However, if the dopant concentration is reduced in the drift tube (e.g., the separation region), the ion clusters will begin to fall apart as they move down the drift tube to the ion collector, decreasing analyte sensitivity. This results in a smaller target ion peak and the formation of multiple cluster fragment peaks. Keeping the dopant concentration high in the drift region promotes reformation of the ion clusters when fragmentation occurs.

This embodiment maintains the dopant reagent concentration high in the separation region 80 and low near the shutter 86 to provide a large and stable target ion peak. Additionally, the air sample flow rate affects the dopant reagent concentration at the ion shutter, with higher flow rates effectively decreasing the dopant concentration at the ion shutter. This allows the dynamic range (and sensitivity) of the analyzer to be adjusted by changing sample flow rate as needed. A multiple concentration range analyzer is provided by any means known in the art that varies sample inflow rate, such as with one or more solenoid valves 230 to switch between different vacuum orifices positioned at the IMS exhaust, for example.

The dopant concentration at the ion collector 110 can be controlled by varying one or more parameters that affect the flux of dopant in the direction of diminishing gradient of dopant by diffusion. Examples of such parameters include, but are not limited to, the dopant permeation module temperature and internal tubing diameter and tubing length of orifice 250 that connects the dopant source to the separation region 80. In an aspect, a combination of diffusion and mass transport (e.g., convection such as by bulk flow of drift gas) provides further control of dopant concentration at the ion collector.

FIGS. 10-14 provide experimental results for a high sensitivity ammonia analyzer, where the dopant is introduced by diffusion only without drift gas. In this aspect, clean dry air (CDA) or pressure regulators are not needed. The sample flow rate is about 228 mL/min and the span is calibrated with 5 ppb ammonia. Such a diffusion-introduced dopant system without drift gas provides a dopant concentration gradient along a transverse direction, where the lower levels of dopant at the shutter grid, while maintaining higher dopant levels toward the ion detector, improves detection limit by about five-fold compared to IMS systems with a drift gas that provides for high dopant levels across the separation region and at the shutter grid. These systems eliminate requirements of CDA, problems associated with CDA contamination, and problems with pressure regulators (e.g., contamination, variation between regulators, cost, etc.). In addition, the diffusion-based dopant introduction further simplifies the equipment and methods, avoiding the need for drift gas and attendant flow-controllers such as fans, pumps, and flow-regulators and associated power requirements.

STATEMENTS REGARDING INCORPORATION BY REFERENCE AND VARIATIONS

All references cited throughout this application, for example patent documents including issued or granted patents or equivalents; patent application publications; and non-patent literature documents or other source material are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, materials, reagents, synthetic methods, purification methods, analytical methods, assay methods, and methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

I claim:

1. An ion mobility spectrometer for detecting an analyte in a gas phase sample, said spectrometer comprising:
   a. an inlet for introducing said gas phase sample containing said analyte to an ionization region having an ionization source;
   b. a source of dopant in fluid communication with said ionization region, wherein said ionization source generates ions from said analyte and dopant;
   c. a separation region in fluid communication with said ionization region and said source of dopant, for receiving and separating said generated ions on the basis of ion mobility; and
   d. a detector positioned in fluid communication with said separation region for receiving and detecting said ions on the basis of ion mobility,
   wherein said dopant in said separation region is in excess, and at a dopant to analyte ratio in the separation region that is greater than 1000, and said dopant is continuously introduced to said separation region thereby providing at least a portion of said separation region with excess dopant.

2. The spectrometer of claim 1, wherein said source of dopant further comprises a drift gas.

3. The spectrometer of claim 1 further comprising a dopant inlet port for introducing dopant to said separation region.

4. The spectrometer of claim 3, wherein said dopant inlet port is positioned in the separation region to introduce dopant directly to the separation region in a direction that is substantially opposite to the ion mobility direction of said ions generated from said analyte and dopant.

5. The spectrometer of claim 1, further comprising a membrane positioned at or upstream of said inlet for removing water vapor or to reduce amount of said analyte introduced to said ionization region.

6. The spectrometer of claim 1, wherein said spectrometer is a membrane-free spectrometer.

7. The spectrometer of claim 1, wherein all or substantially all of said analyte is introduced to said ionization region.

8. The spectrometer of claim 7, wherein said gas phase sample contains water vapor, and wherein substantially all of said water vapor is introduced to said ionization region simultaneously with said analyte.

9. The spectrometer of claim 1, wherein:
   a. said gas phase sample introduction to said ionization region rate has a sample flowrate, and
   b. said dopant introduction to said separation region has a dopant flowrate,
   and said sample flowrate is selected from a range that is between 0.1 to ten times of said dopant flowrate.

10. The spectrometer of claim 9, wherein said dopant inflow is continuous and selected from a range that is between 20 mL/min to 1000 mL/min.

11. The spectrometer of claim 1, wherein said dopant excess has a dopant amount, and said amount in said separation region is selected from a range between $10^4$ to $10^9$ times of said analyte amount in said separation region.

12. The spectrometer of claim 11, wherein said dopant excess in said separation region is at a concentration selected from a range between 0.1 ppm to 500 ppm.

13. The spectrometer of claim 11, wherein said dopant amount is substantially constant throughout said ionization region and said separation region.

14. The spectrometer of claim 11, wherein said dopant amount varies along a longitudinal direction in said separation region, with a dopant minimum amount at a separation region first end that corresponds to a boundary between said separation region and said ionization region.

15. The spectrometer of claim 1, wherein said excess dopant generates dopant-dopant clusters and dopant-analyte dimerization clusters and prevents detectable formation of ion clusters from an interfering substance.

16. The spectrometer of claim 1, wherein
   a. the analyte is selected from the group consisting of amines, hydrazines, chlorine, HCl, HF, $F_2$, $Br_2$, HBr, $NO_x$, $SO_x$, pharmaceutical compounds, chemical warfare agents, ammonia, peroxides, explosive-indicating compounds and narcotic-indicating compounds; and
   b. the dopant is selected from the group consisting of substituted phenols, Dimethyl methylphosphonate, methyl salicylate, 2-hydroxyacetophenone, $SO_2$, and 2-Chlorobutane.

17. The spectrometer of claim 16 wherein the analyte and dopant are selected from the group consisting of:
   a. ammonia and dimethyl methylphosphonate;
   b. $H_2O_2$ and methyl salicylate; and
   c. acid and methyl salicylate.

18. The spectrometer of claim 1, wherein said dopant is introduced to said separation region by diffusion of said dopant from said source of dopant to said separation region, said spectrometer further comprising:
   a. a shutter grid at a first end of said separation region; and
   b. an ion collector at a second end of said separation region;
   wherein said dopant has a concentration gradient along a longitudinal direction with a maximum amount of dopant at said second end and a minimum amount at said first end.

19. The spectrometer of claim 18, wherein said dopant concentration at said ion collector is at least 10 times greater than said dopant concentration at said shutter grid.

20. The spectrometer of claim 18, further comprising an adjustable flow-rate control operably connected to said inlet for introducing gas phase sample containing said analyte at a user-selected flow-rate for adjusting said dopant concentration at said shutter grid to a value that is selected from a range that is between 50 ppb to 500 ppm.

21. An ion mobility spectrometer cell comprising:
   a. an ionization region;
   b. a separation region in fluid communication with said ionization region;
   c. means for introducing an analyte in a gas phase sample to said ionization region; and
   d. means for introducing a dopant in an excess amount to said separation region, wherein said excess amount corresponds to a dopant to analyte ratio in the separation region that is greater than 1000.

22. The cell of claim 21, wherein:
   a. said means for introducing gas phase sample comprises a carrier gas that transports said analyte in a gas phase sample to an ionization inlet positioned adjacent to the ionization region; and
   b. said means for introducing dopant comprises a drift gas that transports said dopant to a separation inlet positioned adjacent to the separation region.

23. The cell of claim 21, wherein said means for introducing dopant comprises:
   a. a holder for holding a source of dopant;
   b. a conduit that connects said holder to said separation region to provide fluid communication between said holder and said separation region; and
   c. a source of dopant disposed in said holder, wherein dopant is introduced to said separation region by diffusion from said holder to said separation region.

24. A method for detecting an analyte in a gas phase sample, said method comprising:
a. providing an ion mobility cell having a separation region and an ionization region, wherein the regions are in fluid communication with each other, said separation region having a first end adjacent to said ionization region and a second end corresponding to an ion detector that is separated from said first end by a longitudinal distance;
b. introducing said analyte in a gas phase sample to said ionization region;
c. introducing a high concentration of dopant to at least said separation region second end;
d. ionizing said analyte and said dopant in said ionization region, thereby generating detectable ions;
e. passing said detectable ions through said separation region, wherein said detectable ions are separated on the basis of ion mobility and said high concentration of dopant in said separation region corresponds to a dopant to analyte ratio in the separation region that is greater than 1000; and
f. detecting said detectable ions separated on the basis of ion mobility with a detector in fluid communication with said separation region, thereby detecting said analyte.

25. The method of claim 24, wherein said analyte is selected from the group consisting of amines, hydrazines, chlorine, HCl, HF, $F_2$, $Br_2$, HBr, $NO_x$, $SO_x$, pharmaceutical compounds, chemical warfare agents, ammonia; peroxides; explosive-indicating compounds and narcotic-indicating compounds.

26. The method of claim 24, wherein the dopant is selected from the group consisting of substituted phenols, dimethyl methylphosphonate, methyl salicylate, 2-hydroxyacetophenone, $SO_2$, and 2-Chlorobutane.

27. The method of claim 24, further comprising introducing a drift gas to said separation region to convey said dopant in said separation to said ionization region.

28. The method of claim 24, further comprising introducing said dopant to said separation region by diffusion, thereby establishing a dopant concentration gradient along a longitudinal direction of said separation region, with a minimum dopant concentration in said separation region at said separation region first end.

29. The method of claim 28, further comprising adjusting an amount of sample introduced to said ionization region to provide a dopant to analyte ratio at the separation region first end that is between 100:1 and 10,000:1.

30. The method of claim 24, wherein the ratio of dopant to analyte in said ionization region is selected from a range that is between 100 to 10,000.

31. A method for detecting an analyte, said method comprising:
a. providing an ion mobility spectrometer comprising;
  i. an inlet for introducing said gas phase sample containing said analyte to an ionization region having an ionization source;
  ii. a source of dopant in fluid communication with said ionization region, wherein said ionization source generates ions from said analyte and dopant;
  iii. a separation region in fluid communication with said ionization region and said source of dopant, for receiving and separating said generated ions on the basis of ion mobility; and
  iv. a detector positioned in fluid communication with said separation region for receiving and detecting said ions on the basis of ion mobility, wherein said dopant in said separation region is in excess, and said dopant is continuously introduced to said separation region thereby providing at least a portion of said separation region with excess dopant;
b. introducing an analyte in a gas phase sample to said ionization region;
c. introducing a dopant in excess to said separation region from said source of dopant, wherein said dopant excess corresponds to a dopant to analyte ratio in the separation region that is greater than 1000;
d. ionizing said analyte in a gas phase sample and dopant in said ionization region to generate detectable ions;
e. introducing said detectable ions to said separation region;
f. separating said detectable ions, and any clusters thereof, on the basis of ion mobility; and
g. detecting said ion mobility by measuring drift time peaks, thereby detecting said analyte.

32. A method of suppressing interference in an ion mobility spectrometer, said method comprising:
a. providing an ion mobility spectrometer having a separation region and an ionization region in fluid communication with each other;
b. introducing a dopant to said separation region, wherein said dopant is provided at an amount in excess of 0.1 ppm;
c. introducing a sample containing an interfering material and an analyte to said ionization region;
d. ionizing said sample thereby generating analyte ions; and
e. introducing said analyte ions to said separation region by applying an electric field,
wherein said dopant provided in excess in said separation region corresponds to a dopant to analyte ratio in the separation region that is greater than 1000 to suppress interference arising from species other than said analyte.

33. A method of selectively detecting an analyte by ion mobility spectrometry, said method comprising:
a. providing an ion mobility spectrometer having a separation region and an ionization region in fluid communication with each other;
b. introducing a dopant to said separation region, wherein said dopant is provided at an amount in excess of 0.1 ppm;
c. introducing a sample containing an analyte to said ionization region;
d. ionizing said sample thereby generating analyte ions;
e. establishing an electric field in the separation region to introduce said analyte ions to said separation region;
f. detecting said analyte ions separated on the basis of ion mobility with a detector in fluid communication with said separation region,
wherein said dopant provided in excess in said separation region corresponds to a dopant to analyte ratio in the separation region that is greater than 1000 to suppress interference arising from species other than said analyte.

34. The spectrometer of claim 3, wherein said separation region has a first end adjacent to said ionization region and a second end corresponding to said detector that is separated from said first end by a longitudinal distance, wherein said dopant inlet port is located at said second end of said separation region.

35. The spectrometer of claim 1, wherein the dopant to analyte ratio in the separation region is between $10^3$ and $10^{10}$.

36. The spectrometer of claim 1, wherein an interfering peak amplitude generated by an interfering compound is reduced at least 50% compared to the spectrometer without dopant in the separation region.

* * * * *